(12) United States Patent
Thompson et al.

(10) Patent No.: US 6,432,976 B1
(45) Date of Patent: Aug. 13, 2002

(54) 8-AZA-BICYCLO[3.2.1]OCTANE NMDA/NR2B ANTAGONISTS

(75) Inventors: Wayne Thompson, Lansdale; David A. Claremon, Maple Glen; Peter M. Munson, Harleysville; Brian Phillips, Telford, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/696,503

(22) Filed: Oct. 25, 2000

Related U.S. Application Data

(60) Provisional application No. 60/162,718, filed on Oct. 29, 1999.

(51) Int. Cl.[7] .................. A61K 31/46; C07D 401/06
(52) U.S. Cl. .............................. 514/304; 546/126
(58) Field of Search .................... 546/126; 514/304

(56) References Cited

U.S. PATENT DOCUMENTS

| | | |
|---|---|---|
| 4,213,994 A | 7/1980 | Gebert et al. |
| 4,695,575 A | 9/1987 | Janssens et al. |
| 4,820,757 A | 4/1989 | Spang et al. |
| 5,306,723 A | 4/1994 | Chenard |
| 5,436,255 A | 7/1995 | Butler |
| 5,714,498 A | 2/1998 | Kulagowski et al. |
| 5,817,756 A | 10/1998 | Kyle et al. |
| 5,889,019 A | 3/1999 | Mitch |

FOREIGN PATENT DOCUMENTS

| | | |
|---|---|---|
| EP | 0 441 506 B1 | 7/1994 |
| EP | 0 787 493 A1 | 8/1997 |
| WO | WO91/17156 | 11/1991 |
| WO | WO92/19502 | 11/1992 |
| WO | WO93/02052 | 2/1993 |
| WO | WO94/29571 | 12/1994 |
| WO | WO95/28057 | 10/1995 |
| WO | WO96/37226 | 11/1996 |

OTHER PUBLICATIONS

J.D. Kristensen, et al., Pain, 51:249–253(1992).
K. Eida, et al., Pain,61:221–228(1995).
D.J. Knox, et al., Anaesth. Intensive Care, 23:620–622(1995).
M.B. Max, et al., Clin Neuropharmaco., 18:360–368(1995).
I. Ishii, et al., J. Biol. Chem. 268:2836–2843(1993).
A. Wenzel, et al., Neuro Report, 7:45–48(1995).
D.J. Laurie, et al., Mol. Brain Res., 51:23–32(1997).
S. Boyce, et al., Neuropharmacology, 38:611–623(1999).
Z.–L. Zhou et al., J. Med. Chem., 42:2993–3000(1999).
T.F. Gregory, et al., Poster #94, 218th Nat'l Meeting Am. Chem. Soc., New Orleans, Louisiana, Aug. 22–26, 1999.
J.N.C. Kew, et al., Brit. J. Parmacol., 123;463(1998).

*Primary Examiner*—Patricia L. Morris
(74) *Attorney, Agent, or Firm*—Shu M. Lee; David L. Rose

(57) ABSTRACT

Novel 3-substituted 8-aza-bicyclo[3.2.1]octanes (commonly known as "tropanes") substituted in the 8-position are effective as NMDA NR2B antagonists useful for relieving pain.

4 Claims, No Drawings

8-AZA-BICYCLO[3.2.1]OCTANE NMDA/NR2B ANTAGONISTS

This application claims benefit of provisional application Ser. No. 60/162,718, filed Oct. 29, 1999.

BACKGROUND OF THE INVENTION

Field of the Invention

This invention relates to novel 8-aza-bicyclo[3.2.1] octanes. In particular, this invention relates to novel 3-substituted 8-aza-bicyclo[3.2.1]octanes substituted in the 8-position that are effective as NMDA NR2B antagonists useful for relieving pain.

Ions such as glutamate play a key role in processes related to chronic pain and pain-associated neurotoxicity—primarily by acting through N-methyl-D-aspartate ("NMDA") receptors. Thus, inhibition of such action—by employing ion channel antagonists, particularly NMDA antagonists—can be beneficial in the treatment and control of pain.

Known NMDA antagonists include ketamine, dextromophan, and 3-(2-carboxypiperazin-4-yl)-propyl-1-phosphonic acid ("CPP"). Although these compounds have been reported to produce symptomatic relief in a number of neuropathies including postherpetic neuralgia, central pain from spinal cord injury, and phantom limb pain, (J. D. Kristensen, et al., *Pain*, 51:249–253 (1992); K. Eide, et al., *Pain*, 61:221–228 (1995); D. J. Knox, et al., *Anaesth. Intensive Care* 23:620–622 (1995); and M. B. Max, et al., *Clin. Neuropharmacol.* 18:360–368 (1995)) widespread use of these compounds is precluded by their undesirable side effects. Such side effects at analgesic doses include psychotomimetic effects such as dizziness, headache, hallucinations, dysphoria, and disturbances of cognitive and motor function. Additionally, more severe hallucinations, sedation, and ataxia are produced at doses only marginally higher than analgesic doses. Thus, it would be desirable to provide novel NMDA antagonists that are absent of undesirable side effects or that produces fewer and/or milder side effects.

NMDA receptors are heteromeric assemblies of subunits, of which two major subunit families designated NR1 and NR2 have been cloned. Without being bound by theory, it is generally believed that the various functional NMDA receptors in the mammalian central nervous system ("CNS") are only formed by combinations of NR1 and NR2 subunits, which respectively express glycine and glutamate recognition sites. The NR2 subunit family is in turn divided into four individual subunit types: NR2A, NR2B, NR2C, and NR2D. I. Ishii, et al., *J. Biol. Chem.*, 268:2836–2843 (1993), A. Wenel, et al., *NeutralReport*, 7:45–48 (1995), and D. J. Laurie et al., *Mol. Brain Res.*, 51:23–32 (1997) describe how the various resulting, combinations produce a variety of NMDA receptors differing in physiological and pharmacological properties such as ion gating properties, magnesium sensitivity, pharmacological profile, as well as in anatomical distribution.

For example, while NR1 is found throughout the brain, NR2 subunits are differentially distributed. In particular, it is believed that the distribution map for NR2B lowers the probability of side effects while producing pain relief. For example, S. Boyce, et al., *Neuropharmacology*, 38:611–623 (1999) describes the effect of selective NMDA NR2B antagonists on pain with reduced side-effects. Thus, it would be desirable to provide novel NMDA antagonists that target the NR2B receptor.

International Patent Publication WO94/21615 describes benzimidazole-piperidine compounds utilized as dopamine D4 antagonists. Phenol compounds described as NMDA antagonists are described in U.S. Pat. Nos. 5,306,723 and 5,436,255, and in International Patent Publications WO91/17156, WO92/19502, WO93/02052, WO94/29571, WO95/28057, WO96/37226, and EP 04422506. Benzyl piperidines substituted with phenols or imidazoles are described in Z. -L. Zhou, et al., *J. Medicinal Chemistry*, 42:2993–3000 (1999); T. F. Gregory, et al., Poster #94, 218th National Meeting American Chemical Society, New Orleans, La., August 22–26, 1999. Other NMDA NR2B selective compounds are described in European Patent Publication EP 787493 and *British J. Pharmacol.*, 123:463(1998). However, there continues to be a need for novel NMDA antagonists that target the NR2B receptor.

SUMMARY OF THE INVENTION

The present invention relates to 3-substituted 8-aza-bicyclo[3.2.1]octanes substituted in the 8-position with benzimidazoles, imidazopyridines, phenols orimidazoles either directly or through a C1–C4alkyl, cycloalkyl, hydroxyalkyl, alkoxy or aminoalkyl chain. The present invention also forms novel pharmaceutical compositions utilizing these novel compounds. Further, this invention includes novel methods to treat pain by utilizing the novel compounds.

DETAILED DESCRIPTION OF THE INVENTION

In one aspect, the compounds of this invention are 3-substituted 8-aza-bicyclo[3.2.1]octanes (commonly known as "tropanes") represented by Formula (I):

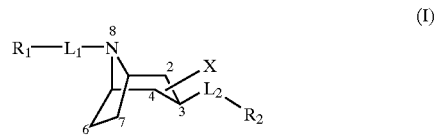

(I)

or pharmaceutically acceptable salts thereof, wherein $R_1$ is benzimidazole, imidazole, imidazopyridine, indole, quinazoline, purine, benzoxazolone, or phenol;

$R_2$ is phenyl, optionally substituted with one to five substituents, each substituent independently being chloro, fluoro, bromo, $C_1$–$C_4$alkyl, trifluoromethyl, hydroxy, or carboxy;

$L_1$ and $L_2$ are independently $C_1$–$C_4$alkyl, $C_1$–$C_4$alkenyl, $C_1$–$C_4$alkynyl, $C_1$–$C_4$alkoxy, amino$C_1$–$C_4$alkyl, hydroxy$C_1$–$C_4$alkyl, carbonyl, cyclo$C_3$–$C_6$alkyl, or aminocarbonyl; and optionally substituted at any of the 2, 3, 4, 6, or 7 positions independently with X, wherein X is hydroxy, amino, $C_1$–$C_4$alkylamino, di($C_1$–$C_4$)alkylamino, $C_1$–$C_4$alkyl, ester, carbamate, carbonate, or ether.

In one embodiment, the compound of this invention is represented by Formula (I) or a pharmaceutically acceptable salt thereof, wherein $R_1$ is benzimidazole;

$R_2$ is phenyl, optionally substituted with one to five substituents, each substituent independently being chloro, fluoro, bromo, $C_1$–$C_4$alkyl, trifluoromethyl, hydroxy, or carboxy;

$L_1$ and $L_2$ are independently $C_1$–$C_4$alkyl, $C_1$–$C_4$alkenyl, $C_1$–$C_4$alkynyl, $C_1$–$C_4$alkoxy, amino$C_1$–$C_4$alkyl, hydroxyC$_1$–C$_4$alkyl, carbonyl, cycloC$_3$–C$_6$alkyl or aminocarbonyl; and optionally substituted at any of the 2, 3, 4, 6, or 7 positions independently with X, wherein X is hydroxy, amino, C$_1$–C$_4$alkylamino, di(C$_1$–C$_4$)alkylamino, C$_1$–C$_4$alkyl, ester, carbamate, carbonate, or ether.

In another embodiment, the compound of this invention is represented by Formula (I) or a pharmaceutically acceptable salt thereof, wherein R$_1$ is imidazole;

R$_2$ is phenyl, optionally substituted with one to five substituents, each substituent independently being chloro, fluoro, bromo, C$_1$–C$_4$alkyl, trifluoromethyl, hydroxy, or carboxy;

L$_1$ and L$_2$ are independently C$_1$–C$_4$alkyl, C$_1$–C$_4$alkenyl, C$_1$–C$_4$alkynyl, C$_1$–C$_4$alkoxy, aminoC$_1$–C$_4$alkyl, hydroxyC$_1$–C$_4$alkyl, carbonyl, cycloC$_3$–C$_6$alkyl or aminocarbonyl; and optionally substituted at any of the 2, 3, 4, 6, or 7 positions independently with X, wherein X is hydroxy, amino, C$_1$–C$_4$alkylamino, di(C$_1$–C$_4$)alkylamino, C$_1$–C$_4$alkyl, ester, carbamate, carbonate, or ether.

In yet another embodiment, the compound of this invention is represented by Formula (I) or a pharmaceutically acceptable salt thereof, wherein R$_1$ is imidazopyridine, R$_2$ is phenyl, optionally substituted with one to five substituents, each substituent independently being chloro, fluoro, bromo, C$_1$–C$_4$alkyl, trifluoromethyl, hydroxy, or carboxy, L$_1$ and L$_2$ are independently C$_1$–C$_4$alkyl, C$_1$–C$_4$alkenyl, C$_1$–C$_4$alkynyl, C$_1$–C$_4$alkoxy, aminoC$_1$–C$_4$alkyl, hydroxyC$_1$–C$_4$alkyl, carbonyl, cycloC$_3$–C$_6$alkyl or aminocarbonyl; and optionally substituted at any of the 2, 3, 4, 6, or 7 positions independently with X, wherein X is hydroxy, amino, C$_1$–C$_4$alkylamino, di(C$_1$–C$_4$)alkylamino, C$_1$–C$_4$alkyl, ester, carbamate, carbonate, or ether.

In still another embodiment, the compound of this invention is represented by Formula (I) or a pharmaceutically acceptable salt thereof, wherein R$_1$ is purine;

R$_2$ is phenyl, optionally substituted with one to five substituents, each substituent independently being chloro, fluoro, bromo, C$_1$–C$_4$alkyl, trifluoromethyl, hydroxy, or carboxy;

L$_1$ and L$_2$ are independently C$_1$–C$_4$alkyl, C$_1$–C$_4$alkenyl, C$_1$–C$_4$alkynyl, C$_1$–C$_4$alkoxy, amino, C$_1$–C$_4$alkyl, hydroxyC$_1$–C$_4$alkyl, carbonyl, cycloC$_3$–C$_6$alkyl or aminocarbonyl; and optionally substituted at any of the 2, 3, 4, 6, or 7 positions independently with X, wherein X is hydroxy, amino, C$_1$–C$_4$alkylamino, di(C$_1$–C$_4$)alkylamino, C$_1$–C$_4$alkyl, ester, carbamate, carbonate, or ether.

In another embodiment, the compound of this invention is represented by Formula (I) or a pharmaceutically acceptable salt thereof, wherein R$_1$ is phenol;

R$_2$ is phenyl, optionally substituted with one to five substituents, each substituent independently being chloro, fluoro, bromo, C$_1$–C$_4$alkyl, trifluoromethyl, hydroxy, or carboxy;

L$_1$ and L$_2$ are independently C$_1$–C$_4$alkyl, C$_1$–C$_4$alkenyl, C$_1$–C$_4$alkynyl, C$_1$–C$_4$alkoxy, aminoC$_1$–C$_4$alkyl, hydroxyC$_1$–C$_4$alkyl, carbonyl, cycloC$_3$–C$_6$alkyl or aminocarbonyl; and optionally substituted at any of the 2, 3, 4, 6, or 7 positions independently with X, wherein X is hydroxy, amino, C$_1$–C$_4$alkylamino, di(C$_1$–C$_4$)alkylamino, C$_1$–C$_4$alkyl, ester, carbamate, carbonate, or ether.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

Unless otherwise stated, the terms "carbonyl" and "aminocarbonyl" include short C$_1$–C2 termini. The terms include, for example, —CH$_2$CONH—, —CH$_2$CO—, —C$_2$H$_4$CONHCH$_2$—, and —CH$_2$COC$_2$H$_4$—.

Unless otherwise stated, the term "carbamate" is used to include —OCOOC$_1$–C$_4$alkyl, —NHCOOC$_1$–C$_4$alkyl, and —OCONHC$_1$–C$_4$alkyl.

The term "halogen" includes fluorine, chlorine, bromine and iodine atoms.

The term "SEM" is used to describe —CH$_2$—O—CH$_2$CH$_2$—Si(CH$_3$)$_3$.

The term "C$_0$" means that the carbon is not present. Thus, "C$_0$–C$_5$" means that there are from none to five carbons present—that is, five, four, three, two, one, or no carbons present.

The term "optionally substituted" is intended to include both substituted and unsubstituted. Thus, for example, optionally substituted aryl could represent a pentafluorophenyl or a phenyl ring.

Compounds described herein contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium,. calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-di benzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set Out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 1 mg to about 500 mg of the active ingredient and each cachet or capsule preferably containing from about 1 to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

EXPERIMENTAL PROTOCOLS

Assessing the Activity of Selected Compounds to Inhibit NR1A/2B NMDA Receptor Activation (FLIPR Assay)

The activity of selected compounds to inhibit NR1A/2B NMDA receptor activation measured as NR1A/2B receptor-mediated $Ca^{2+}$ influx is assessed by the following procedure:

NR1A/2B receptor transfected L(tk) cells are plated in 96-well format at $3 \times 10^6$ cells per plate and grown for one–two days in normal growth media (Dulbeccos MEM with Na pyruvate, 4500 mg glucose, pen/strep, glutamine, 10% FCS and 0.5 mg/ml geneticin). NR1A/2B-expression in these cells is induced by the addition of 4 nM dexamethasone in the presence of 500 μM ketamine for 16–24 hours. After receptor induction cells are washed using a Labsystem Cellwasher two times with assay buffer (Hanks balanced salt solution (HBSS-$Mg^{++}$ free) containing 20 mM HEPES, 0.1% BSA, 2 mM $CaCl_2$ and 250 μM probenecid). The cells of each 96 well cell plate are loaded with the $Ca^{++}$ sensitive dye Fluo-3 (Molecular Probes, Inc.) at 4 μM in assay buffer containing 0.5% FBS, and 0.04% pluronic F-127 (Molecular Probes, Inc.) for 1 h at 37° C. avoiding light. The cells are then washed with the Cellwasher four times with assay buffer leaving them in 100 μl buffer. Test compounds in solution are pipetted by FLIPR (Fluorometric Imaging Plate Reader) into each test well for a 2 min pretreatment. During this time the fluorescence intensity is recorded (excitation at 488 nm and emission at 530 nm). The glutamate/glycine 50 μL agonist solution (final concentration 1 μM/1 μM) is then added by FLIPR into each well already containing 150 μL of buffer (containing the test compound or vehicle) and the fluorescence is continuously monitored for 10 min. The endpoint fluorescence values are used to determine an $IC_{50}$ value comparing the agonist-stimulated signal for the vehicle alone sample and that for the cells incubated with each concentration of test compound.

Determining the Apparent Dissociation Constant (Ki) of Compounds for Human NR1A/NR2B Receptors (Binding Assay)

The radioligand binding assay is performed at room temperature in 96-well microtiter plates with a final assay volume of 1.0 mL in 20 mM Hepes buffer (pH 7.4) containing 150 mM NaCl. Solutions of test compounds were prepared in DMSO and serially diluted with DMSO to yield 20 μL of each of 10 solutions differing by 3-fold in concentration. Non-specific binding (NSB) using hot AMD-1 (10 μM final concentration) and total binding (TB) by using DMSO (2% final concentration). A solution of NR1A/NR2B receptors (40 μM final concentration) and tritiated AMD-2 (1 nM final concentration) were added to the test compounds. After 3 h of incubation at room temperature, samples are filtered through Packard GF/B filters (presoaked in 0.05% PEI, polyethyleninine Sigma P-3143) and washed 10 times with 1 mL of cold 20 mM Hepes buffer per wash. After vacuum drying of the filter plates, 40 μL of Packard Microscint-20 was added and bound radioactivity determined in a Packard TopCount. The apparent dissociation constant (Ki), the maximum percentage inhibition ($\%I_{max}$), the minimum percentage inhibition ($\%I_{min}$) and the hill slope (nH) were determined by a non-linear least squares fitting the bound CPM data to Equation #1 below.

Equation #1:

$$CPM \text{ Bound} = \frac{(SB)(\% I_{max} - \% I_{min})}{(1 + ([Drug]/(Ki[L - 844,345]/K_D))^{nH})} + NSB + (SB)(1 - \% I_{max})$$

where, $K_D$ is the apparent dissociation constant for the radioligand for the receptor as determined by hot saturation and SB is the specifically bound CPM determined from the difference of TB and NSB.

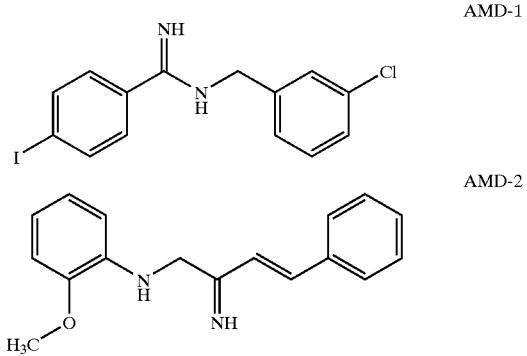

AMD-1

AMD-2

Compounds AMD-1 and AMD-2 can be synthesized in accordance with the following general reaction schemes.

SCHEME 1

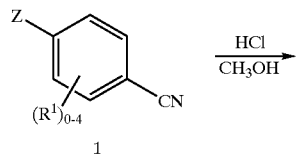

1

-continued

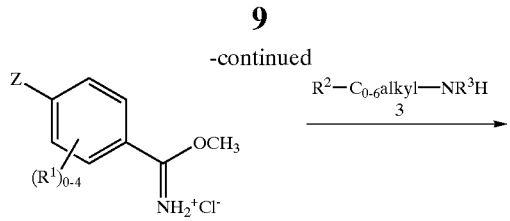

In accordance with scheme 1, hydrogen chloride is bubbled through a solution of the appropriately substituted benzonitrile 1 in methanol at room temperature. The volatiles are removed under reduced pressure and the resulting residue is triturated with ether and filtered to yield the desired imidate 2. Imidate 2 is dissolved in methanol at ambient temperature, treated with amine 3 at ambient temperature and stirred under argon. The volatiles are removed under reduced pressure and the residue purified by preparative HPLC or trituration with ether to afford amidine Ia.

SCHEME 2

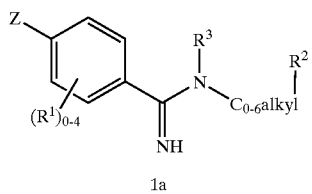

In accordance with scheme 2, at room temperature under argon, amine 3a is dissolved in ether and was treated with 1-M hydrogen chloride in ether (1 equiv.) in a single portion. The resulting precipitate is stirred vigorously for 10 minutes. The volatiles are removed under reduced pressure. The residue is suspended in toluene, cooled to 0° C. under argon, treated with 2.0-M trimethylaluminum (1.05 equiv.) in a dropwise manner, and stirred for 45 minutes at room temperature to afford intermediate 6 (not isolated). Compound 6 is added to a solution of nitrile 1 in toluene. The reaction is heated to 80° C. without stirring in a sealed tube for 18 h, cooled to ambient temperature, poured onto a silica gel column and eluted with methanol/dichloromethane to give the amidine 4.

Preparation of [$^{125}$I]AMD-1

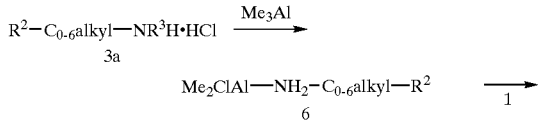

-continued

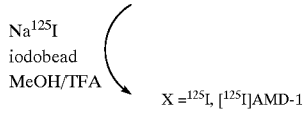

Tritiated AMD-1 was prepared by the following procedure: A mixture of AMD-1, hydrochloride salt, (5 mg, 0.012 mmol) in dioxane (0.2 mL) containing triethylamine (4 μL) was treated with hexamethylditin (5 μL), a catalytic amount of palladium catalyst and heated at 100° C. for 45 minutes. The reaction was cooled to room temperature, filtered through a glass wool plug, rinsed with methanol and concentrated in vacuo to give 10.7 mg of a brown oil. The oil was dissolved in methylene chloride and passed through a small silica column eluting with methylene chloride followed by 5% methanol/methylene chloride. Fractions containing the trimethylstannane (Rf 0.26 in 10% methanol/methylene chloride) were pooled and concentrated in vacuo to give 4.5 mg of the trimethylstannane as a clear colorless oil. This material was further purified by HPLC (C18 Econosil, 10×250 mm, 20 minute linear gradient, 30% MeCN:70% H$_2$O (0.1% TFA) to 90% MeCN, 3 mL/min, 254 nm, retention time 15 minutes) to give 3 mg of the trimethylstannane.

A Na$^{125}$I shipping vial (10 mCi, Amersham) was charged with a stir bar, an iodobead, 50 μL of methanol and stirred five minutes at room temperature. A solution of the trimethylstannane (0.1 mg) in 50 μL of methanol containing 5 μL of trifluoroacetic acid was added and the reaction was stirred for five minutes. The reaction was quenched with 50 μL of ammonium hydroxide and purified by HPLC (C18 Vydac protein and peptide column, 4.6×250 mm, 20 minute linear gradient, 30% MeCN:70% H$_2$O (0.1% TFA) to 90% MeCN, 1 mL/min, retention time 11 minutes). Fractions containing the radioactive product were pooled and concentrated in vacuo to give 989 μCi of [$^{125}$I]AMD-1 with a specific activity of 898Ci/mmol as measured by UV absorbance at 272 nm.

Synthesis of Tritiated AMD-2

Tritiated AMD-2 was prepared by the following procedure: The phenol of AMD-2 (2 mg, 0.008 mmol) dissolved in dimethylformamide (0.6 mL) and potassium carbonate (1.2 mg) for 1 hr. High specific activity tritiated methyl iodide (50 mCi, 0.0006 mmol, in toluene 1 mL, American Radiolabeled Chemicals) was added at room temperature and stirred for 2 hours. The reaction mixture was filtered using a Whatman PTFE 0.45 μm syringeless filter device to remove any insoluable potassium carbonate, washed with Abs. ethanol (2 mL, Pharmco), and the combined filtrates were concentrated to dryness at room temperature using a rotary evaporator; this also removed any unreacted tritiated methyl iodide. The residue was purified by HPLC chromatography on a Phenomenx Luna C8 semi-prep column (Luna 5 micro C8(2), 250×10.0 mm) using a gradient system of 20/80 acetonitrile/water with 0.1% trifluoroacetic acid to 100% acetonitrile with 0.1% trifluoroacetic acid in 20 min. Total activity of the product was 8 mCi. Further purification was effected by absorption onto a Waters C-18 Sep-pak column (Waters Sep-Pak PLUS C18) and elution with water followed by absolute ethanol. The product was diluted with absolute ethanol (10 mL) before submission for final analysis.

The compounds of this invention exhibit less than 50 μM in the FLIBR and binding assays. Thus, the compounds and pharmaceutical compositions of this invention have been found to exhibit biological activity as NMDA NR2B antagonists. Accordingly, another aspect of the invention is the treatment of pain, migraine, depression, anxiety, schizophrenia, Parkinson's disease, or stroke—maladies that are amenable to amelioration through inhibition of NMDA NR2B receptors—by the administration of an effective amount of the compounds of this invention.

The following examples are provided to more fully illustrate the present invention, and are not to be construed as limiting the scope of the claims in any manner.

EXAMPLES

Preparation of 8-substituted Tropanes

In one Example, 8-substituted tropanes were prepared by Scheme 1 shown below:

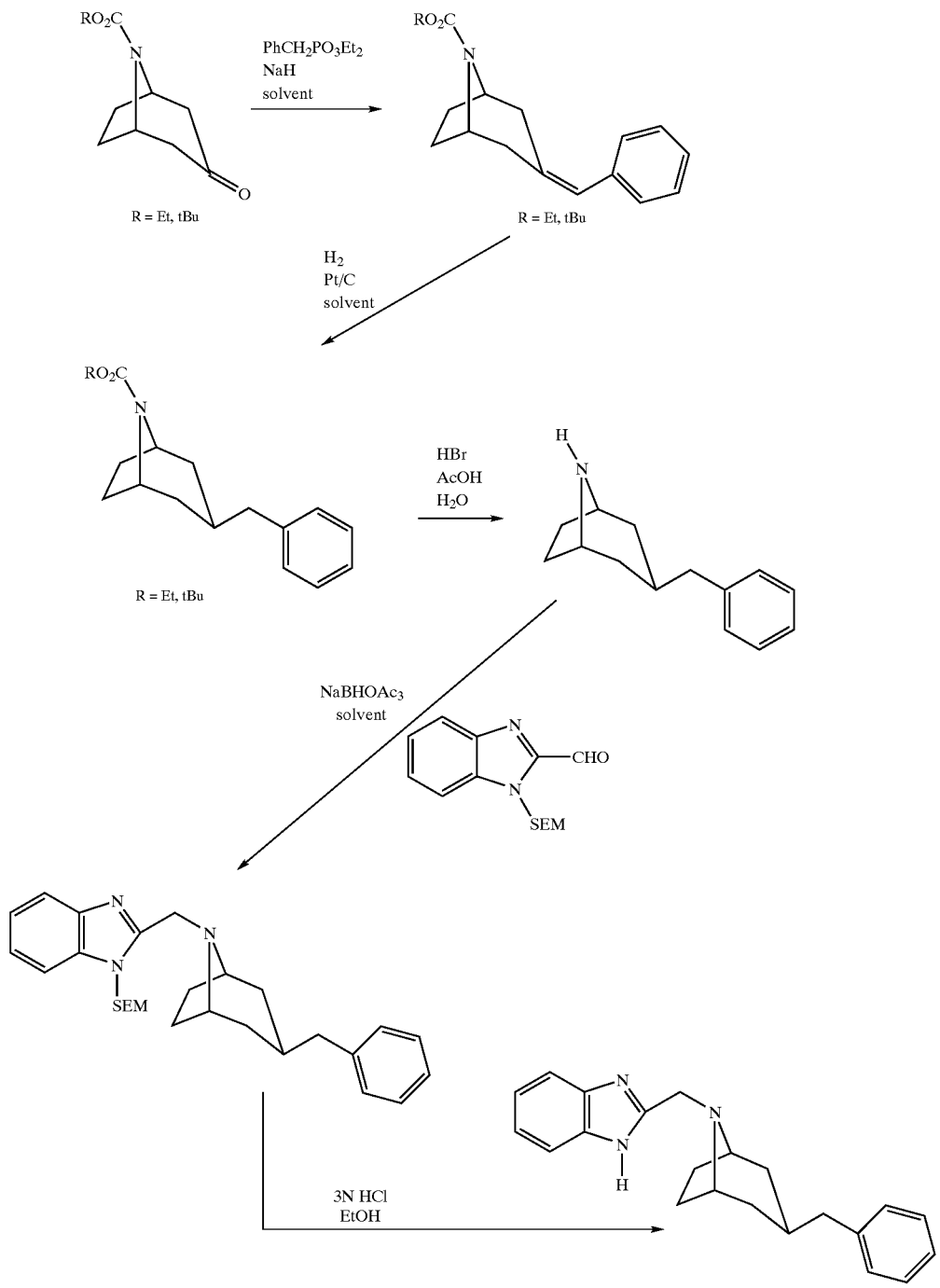

In another Example, 8-substituted tropanes were prepared by Scheme 2 shown below:
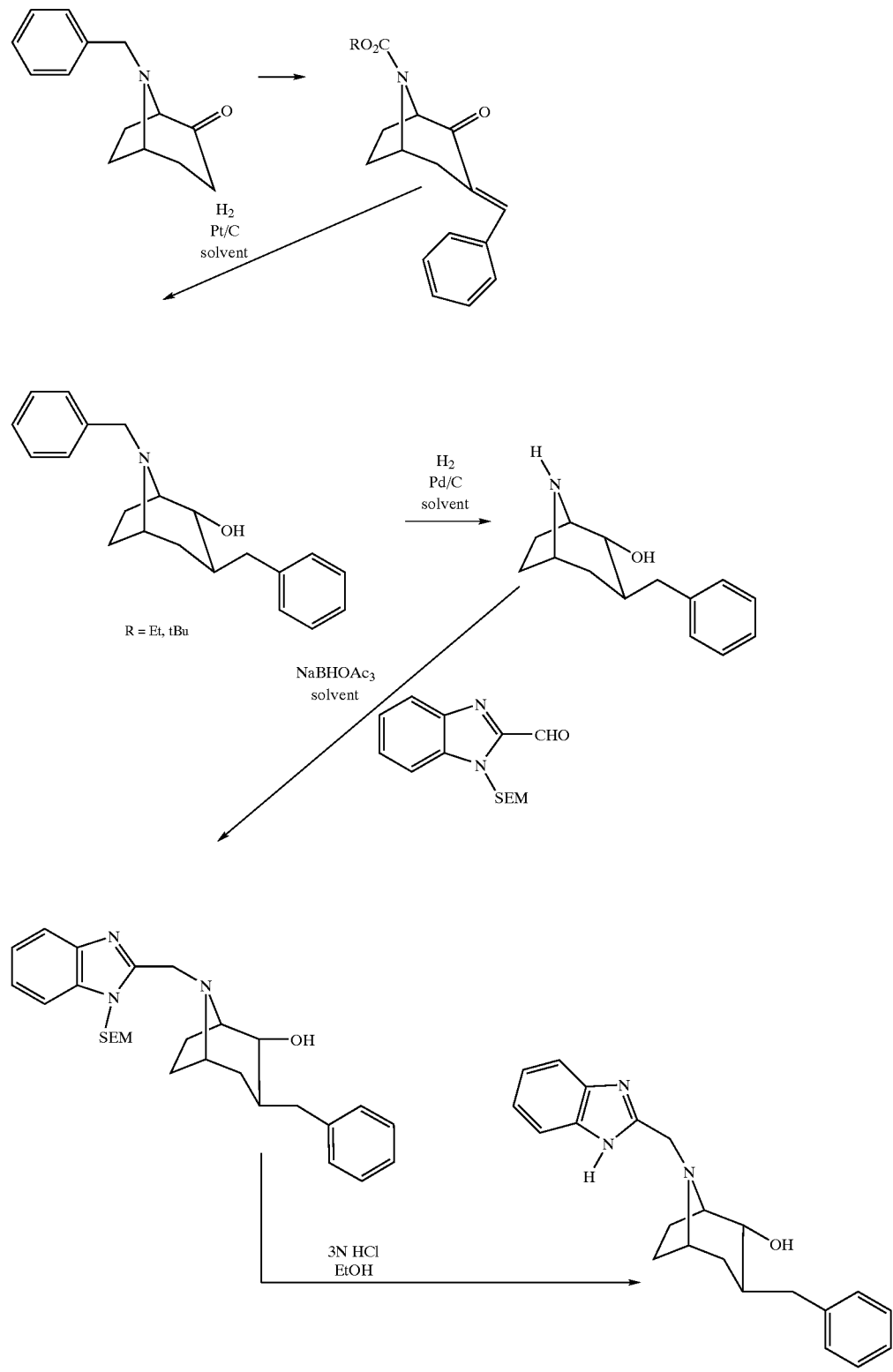

In Schemes 1 and 2 above, in place of the 1-SEM-benzimidole-2-carboxaldehyde

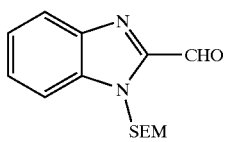

any of the following aldehydes, ketones, or bromides can be used to prepare the compounds of this invention:

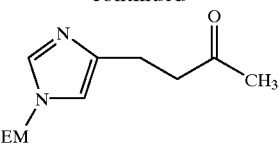

n = 0, 1, 2, 3

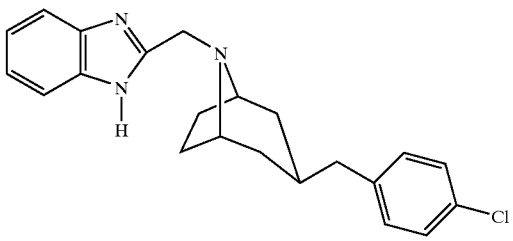

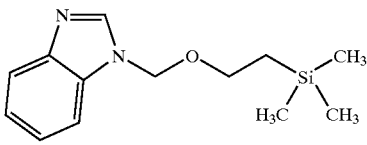

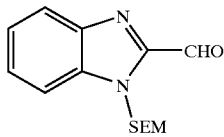

Example 1

2-[3-(4-Chloro-benzyl)-8-aza-bicyclo[3.2.1]oct-8-ylmethyl]-1H-benzimidazole

Example 1 was prepared by the following procedure.

Step 1:

1-(2-Trimethylsilylethoxymethyl)-1H-benzimidazole

A mixture of KH, from 7 g of 30% oil dispersion, and 5 g of benzimidazole in 100 mL of THF was stirred under nitrogen at room temperature for 18 h. To the stirred suspension was added 7 g of 2-trimethylsilylethoxymethyl chloride and the mixture kept at room temperature for 24 h, cooled in an ice bath, cautiously quenched with 50 mL of water, and extracted into ether. The combined ether extracts were dried over $MgSO_4$ and concentrated. Low pressure chromatography over silica gel eluting with a gradient of 3:1 ethyl acetate:hexane to 100% ethyl acetate gave 9.5 g of 1-SEM-benzimidazole as a colorless oil.

Step 2:

1-(2-Trimethylsilylethoxymethyl)-1H-benzimidazole-2-carbaldehyde

To a solution of 40 mmole of lithium diisopropylamide in 100 mL of THF cooled to −78° C. was added 5 g of 1-SEM-benzimidazole in 50 mL of THF. After 1.5 h at or below −70° C., the red solution was quenched by rapid addition of 6 mL of methyl formate. After warming to room temperature over 30 min, 50 mL of water and 200 mL of ethyl acetate were added. The organic layer was separated and dried over MgSO$_4$ then concentrated under reduced pressure to 5.3 g of a thick oil that solidified in the freezer.
Step 3:

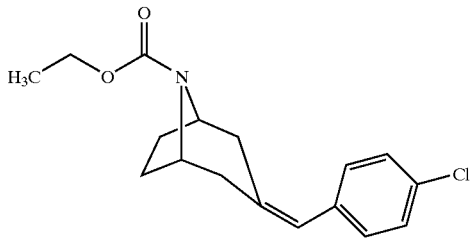

3-(4-Chloro-benzylidene)-8-aza-bicyclo[3.2.1]
octane-8-carboxylic Acid Ethyl Ester To a stirred solution of 2 g of N-carbethoxy-4-tropinone and 3.5 g of diethyl 4-chlorobenzylphosphonate in 10 mL of 1,3-dimethyl-2-imidazolidinone dried over 4 Å mol sieves was added 0.50 g of 60% NaH oil dispersion. The mixture was allowed to stir overnight, diluted with 200 mL of water and extracted with 3×100 mL of ether. Combined extracts were dried over MgSO$_4$ and concentrated under reduced pressure. Low pressure chromatography over silica gel eluting with a gradient of 5:95 ethyl acetate:hexane to 1:5 ethyl acetate:hexane gave 2 g of olefin as a colorless oil.
Step 4:

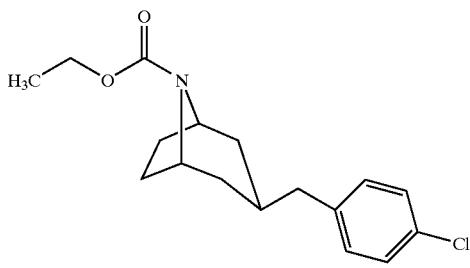

3-(4-Chloro-benzyl)-8-aza-bicyclo[3.2.1]octane-8-
carboxylic Acid Ethyl Ester

A solution of 2 g of 3-(4-chloro-benzylidene)-8-aza-bicyclo[3.2.1]octane-8-carboxylic acid ethyl ester and 0.5 g of 5% platinum on carbon in 100 mL of ethanol was allowed to stir overnight under 1 atm of hydrogen. The catalyst was filtered off and the solution concentrated to give 2 g of a 2:1 mixture of exo:endo isomers of 3-(4-chloro-benzyl)-8-aza-bicyclo[3.2.1]octane-8-carboxylic acid ethyl ester as an oil.
Step 5:

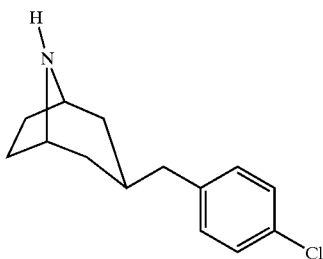

3-(4-Chloro-benzyl)-8-aza-bicyclo[3.2.1]octane

A mixture of 2 g of 3-(4-chloro-benzyl)-8-aza-bicyclo[3.2.1]octane-8-carboxylic acid ethyl ester, 20 mL of 48% HBr and 5 mL of acetic acid was heated to reflux for 2 h. After cooling in an ice bath, the solution was basified to pH 10 by addition of NaOH pellets, extracted with 3×100 mL of chloroform, and the combined extracts dried over MgSO$_4$. Removal of solvents under reduced pressure gave 1.5 g of 2:1 exo:endo 3-(4-chloro-benzyl)-8-aza-bicyclo[3.2.1] octane as a thick oil.
Step 6:

2-[3-(4-Chloro-benzyl)-8-aza-bicyclo[3.2.1]oct-8-
ylmethyl]-1H-benzimidazole

A mixture of 0.5 g of 3-(4-chloro-benzyl)-8-aza-bicyclo [3.2.1]octane, 0.5 g of 1-(2-trimethylsilylethoxymethyl)-1H-benzimidazole-2-carbaldehyde, 5 mL of 1,2-dichloroethane and 0.5 g of sodium triacetoxyborohydride was stirred at room temperature for 48 h. The reaction mixture was diluted with 50 mL chloroform and 10 mL saturated aqueous Na$_2$CO$_3$ and the layers separated. The aqueous layer was extracted with 2×25 mL of chloroform and the combined organic layers were dried over magnesium sulfate and concentrated under reduced pressure. The crude SEM ether was heated to reflux in 50 mL of ethanol containing 5 mL of 3N HCl for 2 h, cooled, concentrated and partitioned between 10 ml of saturated aqueous Na$_2$CO$_3$ and 3×25 mL of chloroform. The chloroform extracts were dried over MgSO$_4$ and concentrated. Purification by chromatography eluting with 90:10 CHCl$_3$:MeOH gave 0.75 g of 2-[3-(4-chloro-benzyl)-8-aza-bicyclo[3.2.1]oct-8-ylmethyl]-1H-benzimidazole as a 2:1 mixture of exo:endo isomers. Chromatography on a Chiralpak™ AS column eluting with a 90:10 mixture of hexane with 0.10% diethylamine and isopropanol gave 0.25 g of endo 2-[3-(4-chloro-benzyl)-8-aza-bicyclo[3.2.1]oct-8-ylmethyl]-1H-benzimidazole: RT=5.34 min; MS (m+1)=366; $^1$H NMR (400 MHz, CDCl$_3$ 3.8 (s, 2H), 3.2 (s, 2H), 2.75 (d, 2H), 2.05 (m, 2H), 1.8 (d, 2H).

Later fractions gave 0.5 g of exo 2-[3-(4-chloro-benzyl)-8-aza-bicyclo[3.2.1]oct-8-ylmethyl]-1H-benzimidazole: RT=9 min; MS (m+1)=366; $^1$H NMR (400 MHz, CDCl$_3$) 9.75 (br, 1H), 7.7 (br, 1H), 7.5 (br, 1H), 7.2 (m, 4H), 7.1 (d, 1H), 3.8 (s, 2H), 3.2 (s, 2H), 2.5 (d, 2H), 2.0 (m, 2H), 1.9 (m, 2H).

Example 2

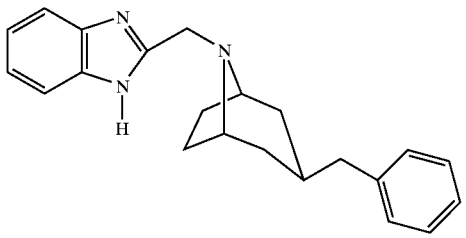

2-(3-Benzyl-8-aza-bicyclo[3.2.1]oct-8-ylmethyl)-
1H-benzimidazole

Example 2 was prepared by following the procedures described above for Example 1, but substituting diethyl benzylphosphonate for diethyl 4-chlorophosphonate. Chromatography on a Chiralpak™ AD column eluting with a 90:10 mixture of hexane with 0.10% diethylamine and isopropanol yielded exo 2-[3-benzyl-8-aza-bicyclo[3.2.1] oct-8-ylmethyl]-1H-benzimidazole: RT 4.6 min; MS (m+1)=332.4; $^1$H NMR (400 MHz, CDCl$_3$) 10 (br, 1H), 7.7

(br, 1H), 7.5 (br, 1H), 7.2 (m, 7H), 3.8 (s, 2H), 3.2 (s, 2H), 2.55 (d, 2H), 2.05 (m, 2H), 1.6 (d, 2H), 1.5 (m, 3H), 1.2 (m, 2H).

Later fractions gave endo 2-[3-benzyl-8-aza-bicyclo[3.2.1]oct-8-ylmethyl]-1H-benzimidazole: RT=6.2 min; MS (m+1)=332.4; ¹H NMR (400 MHz, CDCl₃) 10 (br, 1H), 7.7 (br, 1H), 7.5 (br, 1H), 7.2 (m, 7H), 3.8 (s, 2H), 3.2 (s, 2H), 2.75 (d, 2H), 2.1 (m, 5H), 1.85 (m, 2H), 1.4 (d, 2H).

Example 3

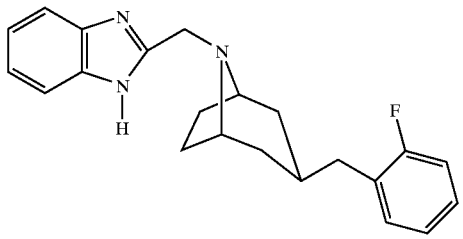

2-[3-(2-Fluoro-benzyl)-8-aza-bicyclo[3.2.1]oct-8-ylmethyl-]-1H-benzimidazole

Example 3 was prepared by following the procedures described above for Example 1, but substituting diethyl 2-fluorobenzylphosphonate for diethyl 4-chlorophosphonate. Chromatography yielded a mixture of exo and endo 2-[3-(2-fluoro-benzyl)-8-aza-bicyclo[3.2.1]oct-8-ylmethyl]-1H-benzimidazole: MS (m+1)=350; ¹H NMR (400 MHz, CDCl₃ 10 (br, 1H), 7.6 (br, 2H), 7.5 (br, 1H), 7.2 (m, 4H), 6.9 (m, 2H), 3.9 (s, 2H), 3.25 (s, 2H), 2.8 (d, 0.6×2H, endo), 2.55 (d, 0.4×2H, exo), 2.2 (m, 4H), 1.9 (d, 2H), 1.7–1.4 (m, 3H).

Example 4

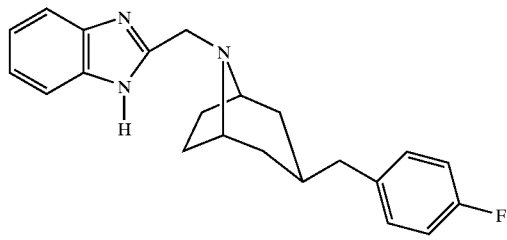

2-[3-(4-Fluoro-benzyl)-8-aza-bicyclo[3.2.1]oct-8-ylmethyl]-1H-benzimidazole

Example 4 was prepared by following the procedures described above for Example 1, but substituting diethyl 4-fluorobenzylphosphonate for diethyl 4-chlorophosphonate. Chromatography on a Chiralpak™ AD column eluting with a 90:10 mixture of hexane with 0.10% diethylamine and isopropanol yielded exo 2-[3-(4-fluoro-benzyl)-8-aza-bicyclo[3.2.1]oct-8-ylmethyl]-1H-benzimidazole: MS (m+1)=350; ¹H NMR (400 MHz, CDCl₃) 10 (br, 1H), 7.7 (br, 1H), 7.5 (br, 1H), 7.2 (m, 7H), 3.8 (s, 2H), 3.2 (s, 2H), 2.55 (d, 2H), 2.05 (m, 2H), 1.6 (d, 2H), 1.5 (m, 3H), 1.2 (m, 2H).

Later fractions gave endo 2-[3-(4-fluoro-benzyl)-8-aza-bicyclo[3.2.1]oct-8-ylmethyl]-1H-benzimidazole: MS (m+1)=350; ¹H NMR (400 MHz, CDCl₃) 10 (br, 1H), 7.8 (br, 1H), 7.45 (br, 1H), 7.25 (m, 2H), 7.15 (m, 2H), 6.95 (m, 2H), 3.82 (s, 2H), 3.2 (s, 2H), 2.70 (d, 2H).

Example 5

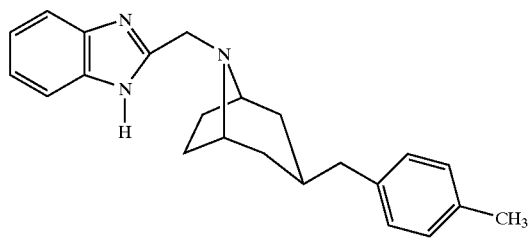

2-[3-(4-Methyl-benzyl)-8-aza-bicyclo[3.2.1]oct-8-ylmethyl]-1H-benzimidazole

Example 5 was prepared by following the procedures described above for Example 1, but substituting diethyl 4-methylbenzylphosphonate for diethyl 4-chlorophosphonate. Chromatography on a Chiralpak™ column eluting with a 90:10 mixture of hexane with 0.10% diethylamine and isopropanol gave endo 2-[3-(4-methyl-benzyl)-8-aza-bicyclo[3.2.1]oct-8-ylmethyl]-1H-benzimidazole: RT 17.04 min; MS (m+1)=346; ¹H NMR (400 MHz, CDCl₃) 10 (br, 1H), 7.7 (br, 1H), 7.5 (br, 1H), 7.2 (m, 6H), 3.8 (s, 2H), 3.2 (s, 2H), 2.7 (d, 2H), 2.3 (s, 3H).

Later fractions gave endo 2-[3-(4-methyl-benzyl)-8-aza-bicyclo[3.2.1]oct-8-ylmethyl]-1H-benzimidazole: RT=20.4 min; MS (m+1)=346; ¹H NMR (400 MHz, CDCl₃) 10 (br, 1H), 7.7 (br, 1H), 7.5 (br, 1H), 7.2 (m, 4H), 7.1 (dd, 2H), 3.85 (s, 2H), 3.2 (s, 2H), 2.5 (d, 2H), 2.35 (s, 3H), 2.05 (m, 2H), 1.85 (m, 2H), 1.8–1.6 (m, 4H), 1.48 (m, 1H).

Example 6

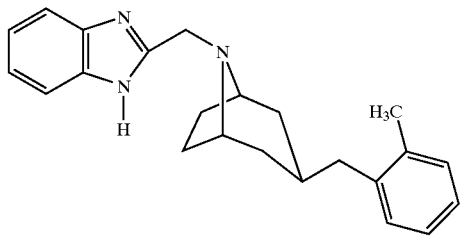

2-[3-(2-Methyl-benzyl)-8-aza-bicyclo[3.2.1]oct-8-ylmethyl]-1H-benzimidazole

Example 6 was prepared by following the procedures described above for Example 1, but substituting diethyl 2-methylbenzylphosphonate for diethyl 4-chlorophosphonate. Chromatography yielded a mixture of exo and endo 2-[3-(2-methyl-benzyl)-8-aza-bicyclo[3.2.1]oct-8-ylmethyl]-1H-benzimidazole: MS (m+1)=346; ¹H NMR (400 MHz, CDCl₃ 10 (br, 1H), 7.6 (br, 2H), 7.5 (br, 1H), 7.2 (m, 5H), 3.95 (s, 2H), 3.30 (br s, 2H), 2.86 (d, 2H), 2.40 (s, 3H).

Example 7

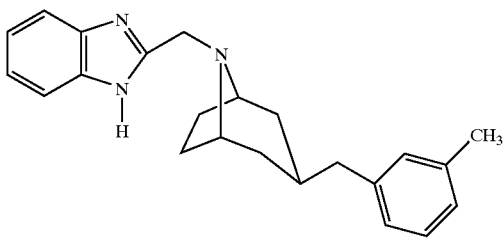

2-[3-(3-Methyl-benzyl)-8-aza-bicyclo[3.2.1]oct-8-ylmethyl]-1H-benzimidazole

Example 7 was prepared following the procedures described above for Example 1, but substituting diethyl 3-methylbenzylphosphonate for diethyl 4-chlorophosphonate. Chromatography yielded a mixture of exo and endo 2-[3-(3-methyl-benzyl)-8-aza-bicyclo[3.2.1]oct-8-ylmethyl]-1H-benzimidazole: MS (m+1)=346.5; $^1$H NMR (400 MHz, CDCl$_3$ 10 (br, 1H), 7.6 (br, 2H), 7.5 (br, 1H), 7.2 (m, 4H), 6.9 (m, 2H), 3.9 (s, 2H), 3.25 (s, 2H), 2.7 (d, 0.6×2H, endo), 2.5 (d, 0.4×2H, exo), 2.3 (2s, 3H), 2.2 (m, 4H), 1.9 (d, 2H), 1.7–1.4 (m, 3H).

Example 8

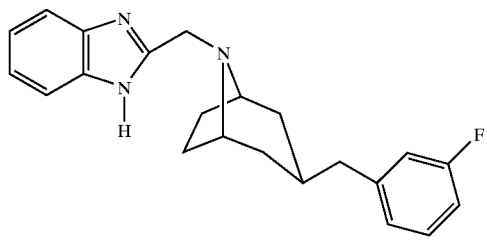

2-[3-(3-Fluoro-benzyl)-8-aza-bicyclo[3.2.1]oct-8-ylmethyl]-1H-benzimidazole

Example 8 was prepared following the procedures described above for Example 1, but substituting diethyl 3-fluorobenzylphosphonate for diethyl 4-chlorophosphonate. Chromatography yielded a mixture of exo and endo 2-[3-(3-fluoro-benzyl)-8-aza-bicyclo[3.2.1]oct-8-ylmethyl]-1H-benzimidazole: MS (m+1)=350; $^1$H NMR (400 MHz, CDCl$_3$ 10 (br, 1H), 7.6 (br, 1H), 7.5 (br, 1H), 7.2 (m, 4H), 6.9 (m, 2H), 3.85 (m, 2H), 3.25 (br s, 2H), 2.75 (d, 0.6×2H, endo), 2.5 (d, 0.4×2H, exo).

Example 9

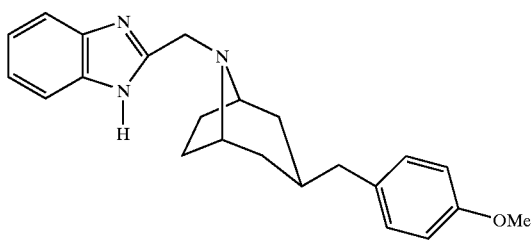

2-[3-(4-Methoxy-benzyl)-8-aza-bicyclo[3.2.1]oct-8-ylmethyl]-1H-benzimidazole Example 9 was prepared by following the procedures described above for Example 1, but substituting diethyl 4-methoxybenzylphosphonate for diethyl 4-chlorophosphonate. Chromatography yielded a mixture of exo and endo 2-[3-(4-methoxy-benzyl)-8-aza-bicyclo[3.2.1]oct-8-ylmethyl]-1H-benzimidazole: MS (m+1)=362; $^1$H NMR (400 MHz, CDCl$_3$ 10 (br, 1H), 7.6 (br, 1H), 7.5 (br, 1H), 7.2 (m, 4H), 7.0 (m, 2H), 3.80 (m, 2H), 3.2 (br s, 2H), 2.7 (d, 0.6×2H, endo), 2.52 (d, 0.4×2H, exo) 2.35 (s, 3H).

Example 10

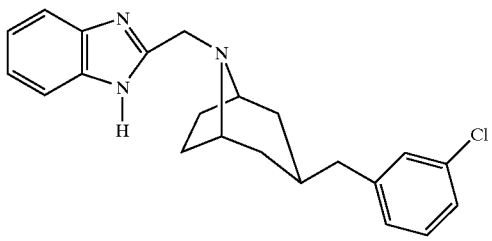

2-[3-(3-Chloro-benzyl)-8-aza-bicyclo[3.2.1]oct-8-ylmethyl]-1H-benzimidazole

Example 10 was prepared by following the procedures described for Example 1, but substituting diethyl 3-chlorobenzylphosphonate for diethyl 4-chlorophosphonate. Chromatography yielded a mixture of exo and endo 2-[3-(3-chloro-benzyl)-8-aza-bicyclo[3.2.1]oct-8-ylmethyl]-1H-benzimidazole: MS (m+1)=366; $^1$H NMR (400 MHz, CDCl$_3$ 10 (br, 1H), 7.6 (br, 1H), 7.5 (br, 1H), 7.2 (m, 4H), 7.0 (m, 2H), 3.80 (m, 2H), 3.2 (br s, 2H), 2.75 (d, 0.6×2H, endo), 2.5 (d, 0.4×2H, exo).

Example 11

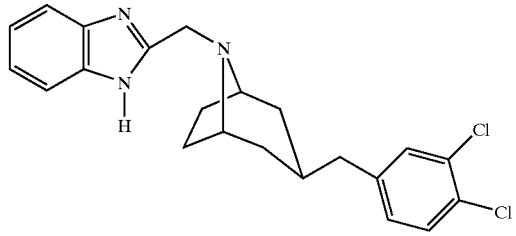

2-[3-(3,4-Dichloro-benzyl)-8-aza-bicyclo[3.2.1]oct-8-ylmethyl]-1H-benzimidazole Example 11 was prepared following the procedures described for Example 1, but substituting diethyl 3,4-dichlorobenzylphosphonate for diethyl 4-chlorophosphonate. Chromatography yielded a mixture of exo and endo 2-[3-(3,4-dichloro-benzyl)-8-aza-bicyclo[3.2.1]oct-8-ylmethyl]-1H-benzimidazole: MS (m+1)=400; $^1$H NMR (400 MHz, CDCl$_3$ 10 (br, 1H), 7.6 (br, 1H), 7.5 (br, 1H), 7.2 (m, 3H), 7.0 (m, 2H), 3.80 (m, 2H), 3.2 (br s, 2H), 2.70 (d, 0.6×2H, endo), 2.5 (d, 0.4×2H, exo).

Example 12

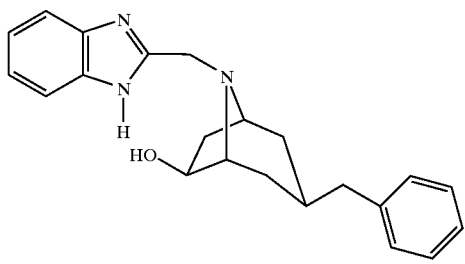

8-(1H-Benzimidazol-2-ylmethyl)-3-benzyl-8-aza-bicyclo[3.2.1]octan-6-ol

Example 12 was prepared by the following procedure.

Step 1:

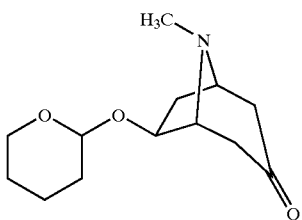

8-Methyl-6-(tetrahydro-pyran-2-yloxy)-8-aza-bicyclo[3.2.1]octan-3-one

A mixture of 1 g of exo-6-hydroxytropinone, 50 mL of methylene chloride and 3 g of dihydropyran was stirred for 3 days. The mixture was diluted with 100 mL of methylene chloride and washed with 50 mL of 1N NaOH. Purification of the residue after concentration by chromatography eluting with a gradient of 190:10:1 to 180:20:5 EtOAc:MeOH:Et$_3$N gave 1.6 g of the THP-ether.

Step 2:

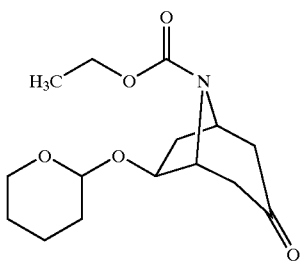

3-Oxo-6-(tetrahydro-pyran-2-yloxy)-8-aza-bicyclo[3.2.1]octane-8-carboxylic Acid Ethyl Ester A mixture of 0.5 g of 8-methyl-6-(tetrahydro-pyran-2-yloxy)-8-aza-bicyclo[3.2.1]octan-3-one, 1 mL of ethyl chloroformate, 25 mg of potassium carbonate, and 10 mL of toluene was heated to reflux overnight. After cooling the mixture was diluted with 500 mL of ether and 50 mL of 3N NaOH and stirred for 2 hours. The organic layer was dried over MgSO$_4$ and concentrated under reduced pressure. Drying under vacuum gave 0.60 g of the ethyl carbamate.

Step 3:

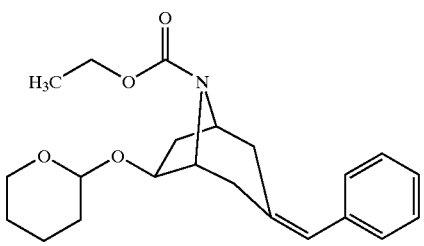

3-Benzylidene-6-(tetrahydro-pyran-2-yloxy)-8-aza-bicyclo[3.2.1]octane-8-carboxylic Acid Ethyl Ester Olefination of 3-oxo-6-(tetrahydro-pyran-2-yloxy)-8-aza-bicyclo[3.2.1]octane-8-carboxylic acid ethyl ester with diethyl phosphonate similarly to the procedure described previously in Step 3 of Example 1, gave 0.3 g of a resin.

Step 4:

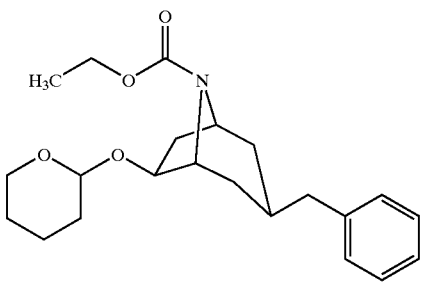

3-Benzyl-6-(tetrahydro-pyran-2-yloxy)-8-aza-bicyclo[3.2.1]octane-8-carboxylic Acid Ethyl Ester Hydrogenation of the 3-benzylidene-6-(tetrahydro-pyran-2-yloxy)-8-aza-bicyclo[3.2.1]octane-8-carboxylic acid ethyl ester similarly to the procedure described in Step 4 of Example 1 over 5% platinum on carbon gave 0.3 g of a resin.

Step 5:

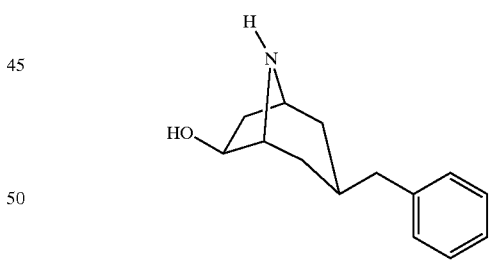

3-Benzyl-8-aza-bicyclo[3.2.1]octan-6-ol

A solution of the 3-benzyl-6-(tetrahydro-pyran-2-yloxy)-8-aza-bicyclo[3.2.1]octane-8-carboxylic acid ethyl ester and 0.5 mL of trimethylsilyl iodide in 25 mL of chloroform was kept at room temperature for 48 h, shaken with 25 mL of 6N NaOH and dilute sodium sulfite and dried over magnesium sulfate. Removal of solvents gave 0.2 g of a resin.

Step 6:

8-(1H-Benzimidazol-2-ylmethyl)-3-benzyl-8-aza-bicyclo[3.2.1]octan-6-ol

The 3-benzyl-8-aza-bicyclo[3.2.1]octan-6-ol was alkylated similarly to the procedure as described for Step 6, Example 1. Separation of the diastereomeric pair of enantiomers was performed on Chiralpak™ AD eluting with 95:5 0.1% diethylamine in hexane:ethanol and gave in order of elution:

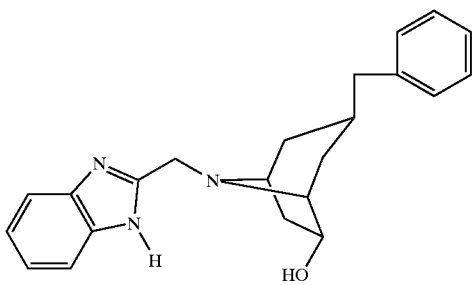

8-(1H-Benzimidazol-2-ylmethyl)-3-exo-benzyl-8-azabicyclo[3.2.1]octan-6-ol enantiomer A: RT=6.7 min, MS (m+1)=348.4, $^1$H NMR (400 MHz, CDCl$_3$) 10.2 (br, 1H), 7.5 (br, 2H), 7.2 (m, 7H), 4.3 (dd, 1H), 4.2 (dd, 2H), 3.4 (d, 1H), 3.15 (s, 1H), 2.5 (d, 2H), 2.15 (m, 1H), 2.0 (m, 1H), 1.7 (m, 1H), 1.5 (m, 3H), 1.3 (m, 1H).

8-(1H-Benzimidazol-2-ylmethyl)-3-exo-benzyl-8-azabicyclo[3.2.1]octan-6-ol enantiomer B: RT=7.3 min, MS (m+1)=348.4, $^1$H NMR (400 MHz, CDCl$_3$) 10.2 (br, 1H), 7.5 (br, 2H), 7.2 (m, 7H), 4.3 (dd, 1H), 4.2 (dd, 2H), 3.4 (d, 1H), 3.15 (s, 1H), 2.5 (d, 2H), 2.15 (m, 1H), 2.0 (m, 11–1), 1.7 (m, 1H), 1.5 (m, 3H), 1.3 (m, 1H).

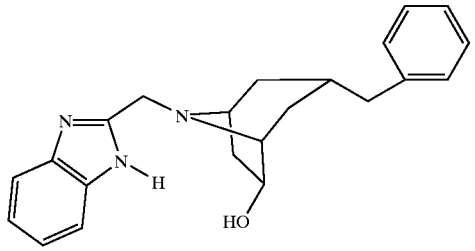

8-(1H-Benzimidazol-2-ylmethyl)-3-endo-benzyl-8-azabicyclo[3.2.1]octan-6-ol enantiomer A: RT=14.0 min, MS (m+1)=348.4, $^1$H NMR (400 MHz, CDCl$_3$) 10.2 (br, 1H), 7.5 (br, 2H), 7.2 (m, 7H), 4.6 (dd, 1H), 4.25 (dd, 2H), 3.4 (s, 1H), 3.15 (s, 1H), 2.7 (d, 2H), 2.42 (dd, 1H), 2.1 (m, 4H), 1.3 (m, 2H).

8-(-1H-Benzimidazol-2-ylmethyl)-3-endo-benzyl-8-azabicyclo[3.2.1]octan-6-ol enantiomer B: RT=15.3 min, MS (m+1)=348.4, $^1$H NMR (400 MHz, CDCl$_3$) 10.2 (br, 1H), 7.5 (br, 2H), 7.2 (m, 7H), 4.6 (dd, 1H), 4.25 (dd, 2H), 3.4 (s, 1H), 3.15 (s, 1H), 2.7 (d, 2H), 2.42 (dd, 1H), 2.1 (m, 4H), 1.3 (m, 2H).

Example 13

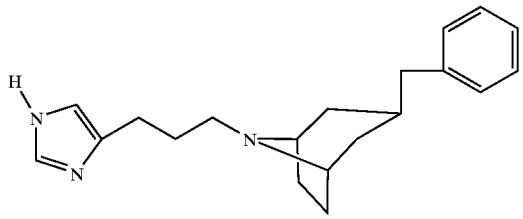

3-Benzyl-8-[3-(1H-imidazol-4-yl)-propyl]-8-azabicyclo[3.2.1]octane

A mixture of 0.25 g of 3-benzyl-8-aza-bicyclo[3.2.1]octane, 0.45 g of 3-(1H-imidazol-4-yl)-propionaldehyde, 5 mL of 1,2-dichloroethane and 0.5 g of sodium triacetoxyborohydride was stirred at room temperature for 48 h. The reaction mixture was diluted with 50 mL chloroform and 10 mL saturated aqueous Na$_2$CO$_3$ and the layers separated. The aqueous layer was extracted with 2×25 mL of chloroform and the combined organic layers dried over magnesium sulfate and concentrated under reduced pressure. Purification by chromatography eluting with 90:10:1 CHCl$_3$:MeOH:NH$_4$OH gave 0.25 g of 3-benzyl-8-[3-(1H-imidazol-4-yl)-propyl]-8-aza-bicyclo[3.2.1]octane as a 2:1 mixture of exo:endo isomers. MS (m+1)=310.3; $^1$H NMR (400 MHz, CDCl$_3$) 7.5–7.1 (complex, 6H), 6.75 (s, 1H), 3.22 (s, 2H), 2.75 (m, 2.6 H), 2.5 (d, 0.7×2H), 2.45 (m, 2H), 2.1 (m, 2H), 1.95 (m, 2H), 1.8 (m, 3H), 1.5 (m, 4H).

Example 14

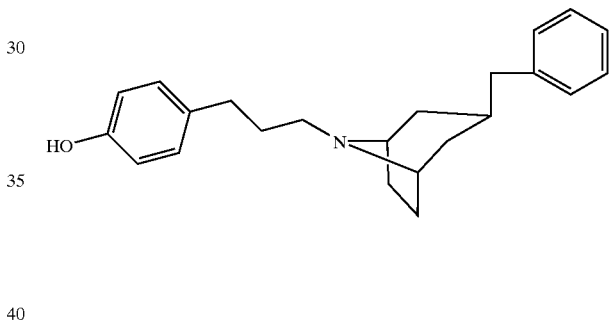

4-[3-(3-Benzyl-8-aza-bicyclo[3.2.1]oct-8-yl)-propyl]-phenol

A mixture of 0.18 g of 3-benzyl-8-aza-bicyclo[3.2.1]octane, 0.30 g of 3-(4-benzyloxy-phenyl)-propionaldehyde, 5 mL of 1,2-dichloroethane and 0.3 g of sodium triacetoxyborohydride was stirred at room temperature for 48 h. The reaction mixture was diluted with 50 mL chloroform and 10 mL saturated aqueous Na$_2$CO$_3$ and the layers separated. The aqueous layer was extracted with 2×25 mL of chloroform and the combined organic layers dried over magnesium sulfate and concentrated under reduced pressure. Purification by chromatography eluting with 80:20 EtOAc:MeOH gave 0.28 g of 3-benzyl-8-[3-(4-benzyloxy-phenyl)-propyl]-8-aza-bicyclo[3.2.1]octane as a 2:1 mixture of exo:endo isomers. Hydrogenation at 1 atm over 0.2 g of 10% Pd/C in 50 mL of ethanol gave 0.17 g of 4-[3-(3-benzyl-8-aza-bicyclo[3.2.1]oct-8-yl)-propyl]-phenol as a 2:1 mixture of exo:endo isomers: MS (m+1)=336.4; $^1$H NMR (400 MHz, CDCl$_3$) 7.25–7.1 (complex, 5H), 6.8 (d, 2H), 6.5 (d, 2H), 3.35 (br s, 2H), 2.75 (d, 0.6 H), 2.5–2.3 (complex, 5.4 H), 2.1 (m, 2H), 1.95 (m, 1H), 1.85 (m, 3H), 1.5 (m, 3H), 1.4 (m, 2H).

Example 15

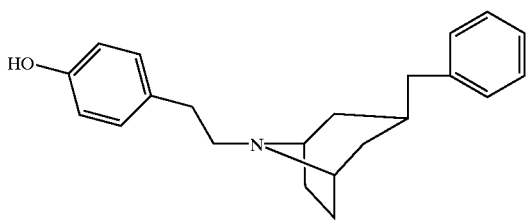

4-[3-(3-Benzyl-8-aza-bicyclo[3.2.1]oct-8-yl)-ethyl]-phenol

Example 15 was prepared in a similar manner to Example 14, 3-(4-benzyloxy-phenyl)-acetaldehyde, gave 4-[3-(3-benzyl-8-aza-bicyclo[3.2.1]oct-8-yl)-ethyl]-phenol as a 2:1 mixture of exo:endo isomers: MS (m+1)=323.2; 1–1H NMR (400 MHz, CDCl$_3$) 7.3–7.15 (complex, 3H), 7.1 (d, 2H), 7.05 (d, 2H), 6.8 (d, 2H), 3.7 (br m, 2H), 3.0 (m, 2H), 2.95 (m, 3H), 2.6 (d, 0.65×2H), 2.4–1.2 (complex, 10).

Example 16

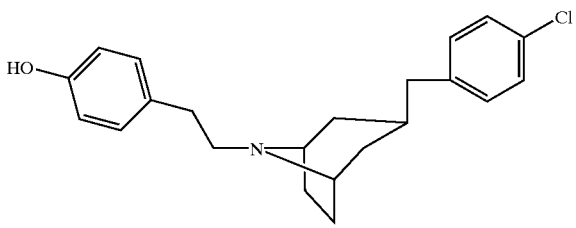

4-{2-[3-(4-Chloro-benzyl)-8-aza-bicyclo[3.2.1]oct-8-yl]-ethyl}-phenol

Example 16 was prepared in a similar manner to Example 15, 3-(1H-imidazol-4-yl)-acetaldehyde, gave 4-{2-[3-(4-chloro-benzyl)-8-aza-bicyclo[3.2.1]oct-8-yl]-ethyl)-phenol as a 2:1 mixture of exo:endo isomers: MS (m+1)=356.2; $^1$H NMR (400 MHz, CDCl$_3$) 7.3–6.95 (complex, 7H), 6.78 (d, 0.65×2H), 6.65 (d, 0.35×2H), 3.4 (br s, 2H), 2.8 (m, 4 H), 2.4–1.2 (complex, 10).

Example 17

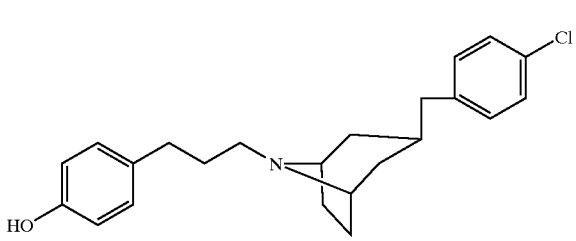

4-{3-[3-(4-Chloro-benzyl)-8-aza-bicyclo[3.2.1]oct-8-yl]-propyl}-phenol

Example 17 was prepared in a similar manner to Example 14, but substituting 3-(4-chloro-benzyl)-8-aza-bicyclo[3.2.1]octane for 3-benzyl-8-aza-bicyclo[3.2.1]octane gave 4-{3-[3-(4-chloro-benzyl)-8-aza-bicyclo[3.2.1]oct-8-yl]-propyl}-phenol as a 2:1 mixture of exo:endo isomers.

Separation by preparative TLC gave endo in the upper band: MS (m+1)=370; $^1$H NMR (400 MHz, CDCl$_3$): 7.3 (m, 2H), 7.05 (t, 2H), 6.85 (d, 2H), 6.6 (d, 2H), 3.7 (br s, 2H), 2.75 (d, 2H), 2.5 (dd, 2H), 1.7 (m, 2H), 1.55 (d, 2H).

The lower band contained the exo isomer: MS (m+1)=370; $^1$H NMR (400 MHz, CDCl$_3$): 7.3 (m, 2H), 7.05 (t, 2H), 6.85 (d, 2H), 6.6 (d, 2H), 3.4 (br s, 2H), 2.75 (d, 1H), 2.5 (m, 4H), 2.1 (m, 2H), 1.9 (m, 4H), 1.7 (m, 2H), 1.55 (d, 2H), 1.4 (d, 2H).

Example 18

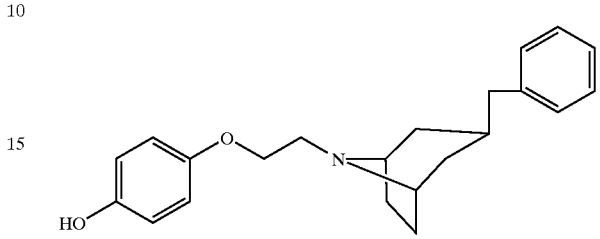

4-[2-(3-Benzyl-8-aza-bicyclo[3.2.1]oct-8-yl)-ethoxy]-phenol

Example 18 was prepared by the following procedure. A mixture of 0.18 g of 3-benzyl-8-aza-bicyclo[3.2.1]octane, 0.30 g of 1-(2-Bromo-ethoxy)-4-benzyloxybenzene, 10 mL of acetonitrile and 0.3 g of potassium carbonate was stirred at reflux for 24 h. The reaction mixture was cooled, concentrated, diluted with 50 μL chloroform and 10 mL saturated aqueous Na$_2$CO$_3$ and the layers separated. The organic layer was dried over magnesium sulfate and concentrated under reduced pressure. Hydrogenation at 1 atm over 0.2 g of 10% Pd/C in 50 mL of ethanol gave 0.17 g of 4-[2-(3-benzyl-8-aza-bicyclo[3.2.1]oct-8-yl)-ethoxy]-phenol as a 2:1 mix of exo:endo isomers after purification by chromatography eluting with 80:20 EtOAc:MeOH: MS (m+1)=338.2; $^1$H NMR (400 MHz, CDCl$_3$) 7.35–6.95 (complex, 5H), 6.76 (d, 2H), 6.6 (d, 2H), 4.1 (m, 2H), 3.5 (br s, 2H), 2.9 (m, 2 H), 2.8 (d, 0.3×2H), 2.54 (d, 0.7×2H), 2.2 (m, 1H), 1.95 (m, 2H), 1.75 (m, 4H), 1.5 (m, 2H).

Example 19

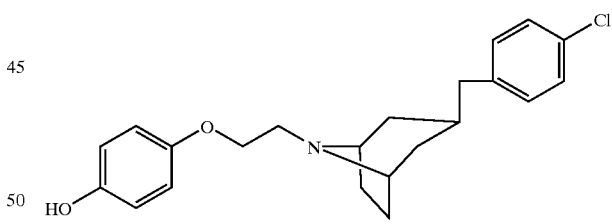

4-{2-[3-(4-Chloro-benzyl)-8-aza-bicyclo[3.2.1]oct-8-yl]-ethoxy}-phenol

Example 19 was prepared in a similar manner to Example 18. 3-(4-chloro-benzyl)-8-aza-bicyclo[3.2.1]octane was substituted for 3-benzyl-8-aza-bicyclo[3.2.1]octane to yield 4-{2-[3-(4-Chloro-benzyl)-8-aza-bicyclo[3.2.1]oct-8yl]-ethoxy}-phenol. Chromatography on a Chiralpak™ column first gave exo 4-{2-[3-(4-chloro-benzyl)-8-aza-bicyclo[3.2.1]oct-8-yl]-ethoxy}-phenol: RT=4.74 min; MS (m+1)=372; $^1$H NMR (400 MHz, CDCl$_3$ 7.25 (d, 2H), 7.05 (d. 2H), 6.70 (s, 4H), 4.05 (t, 2H), 3.3 (br s, 4H), 2.75 (d, 2H), 2.45 (s, 2H), 1.95 (m, 2H), 1.8 (m, 1H), 1.5 (m, 1H).

Later fractions gave 0.5 g of endo 4-{2-[3-(4-chloro-benzyl)-8-aza-bicyclo[3.2.1]oct-8-yl]-ethoxy}-phenol:

RT=6.47 min; MS (m+1)=372; 1H NMR (400 MHz, CDCl$_3$) 7.25 (d, 2H), 7.05 (d. 2H), 6.70 (s, 4H), 4.1 (t, 2H), 3.45 (br s, 4H), 2.95 (t, 2H), 2.8 (d, 2H), 1.90 (d, 2H).

Example 20

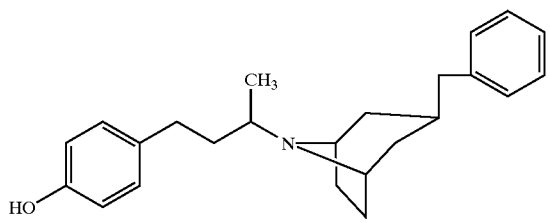

4-[3-(3-Benzyl-8-aza-bicyclo[3.2.1]oct-8-yl)-butyl]-phenol

Example 20 was prepared in a similar manner to Example 14. Substituting 4-(4-hydroxy-phenyl)-butan-2-one in place of 3-benzyl-8-aza-bicyclo[3.2.1]octane yielded 4-[3-(3-benzyl-8-aza-bicyclo[3.2.1]oct-8-yl)-butyl]-phenol as a 2:1 mixture of exo:endo isomers: MS (m+1)=350.5; $^1$H NMR (400 MHz, CDCl$_3$) 7.35–7.2 (complex, 5H), 7.15 (dd, 2H), 6.94 (d, 1H), 6.82 (d, 1H), 3.8 (m, 2H), 3.5 (br s, 2H), 2.85 (m, 2 H), 2.85 (m, 2H), 2.54 (m, 2H), 2.4–2.0 (m, 1H), 1.5 (d, 3H), 1.8–1.1 (complex, 7H).

Example 21

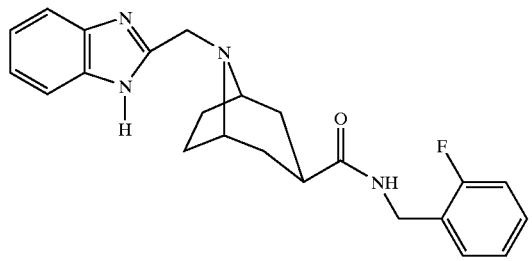

8-(1H-Benzimidazol-2-ylmethyl)-8-aza-bicyclo[3.2.1]octane-3-carboxylic Acid 2-Fluoro-benzylamide Example 21 was prepared by the following procedure.
Step 1:

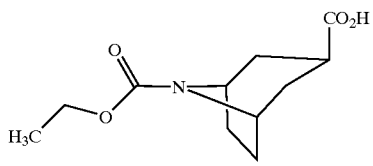

8-Aza-bicyclo[3.2.1]octane-3,8-dicarboxylic Acid 8-Ethyl Ester

Following the general procedure described in U. Schöllkopf and R. Schroeder, Angew. Chem. Int. Ed., 11:311–312(1972), a solution of 2 g of 1-isocyanomethanesulfonyl-4-methyl-benzene in 10 mL of THF was added dropwise to an ice cooled suspension of 1.2 g of potassium tert-butoxide in 20 mL of THF. After cooling to −10° C., a solution of 1.7 g of N-carbethoxytropinone in 10 mL of THF was added over 5 min, and the solution stirred for 15 min at 0° C. The reaction was quenched with 0.6 g of acetic acid and the solvent removed under reduced pressure. The residue was partitioned between 25 mL of water and 50 mL of methylene chloride, dried over magnesium sulfate and concentrated. The dark oily residue was refluxed in 20 mL of 2N HCl for 12 h, cooled, basified with 6N NaOH and washed with 25 mL of ether. The aqueous layer was acidified to pH 1 with conc. HCl, extracted into 3×50 mL of ether and the extracts dried over magnesium sulfate. Removal of solvents under reduced pressure gave 0.55 g of an amber resin.

Step 2:

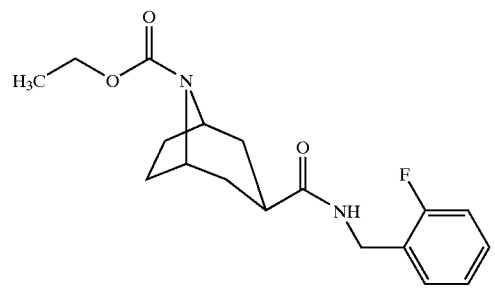

3-(2-Fluoro-benzylcarbamoyl)-8-aza-bicyclo[3.2.1]octane-8-carboxylic Acid Ethyl Ester A mixture of 100 mg of 8-aza-bicyclo[3.2.1]octane-3,8-dicarboxylic acid 8-ethyl ester, 0.056 g of HOBt, 0.074 g of EDC, 0.073 mL of triethylamine, 100 mg of 2-fluorobenzylamine and 5 mL of DMF was stirred at room temperature for 24 h, diluted with 50 mL of 1N HCl and extracted into 3×25 mL of ethyl acetate. The combined organic extracts were washed with 50 mL of saturated sodium carbonate and dried over magnesium sulfate. Removal of solvents under reduced pressure gave 150 mg of a resin.

Step 3:

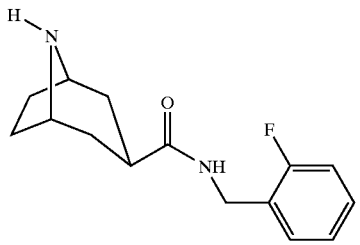

8-Aza-bicyclo[3.2.1]octane-3-carboxylic Acid 2-Fluoro-benzylamide

A solution of 0.15 g of 3-(2-fluoro-benzylcarbamoyl)-8-aza-bicyclo[3.2.1]octane-8-carboxylic acid ethyl ester and 0.5 mL of trimethylsilyl iodide in 25 mL of chloroform was kept at room temperature for 48 h, shaken with 25 mL of 6N NaOH and dilute sodium sulfite and dried over magnesium sulfate. Removal of solvents gave 0.09 g of a resin.

Step 4:

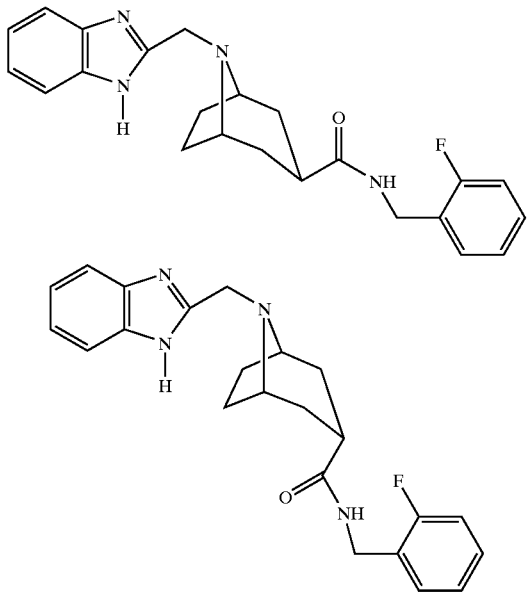

8-(1H-Benzimidazol-2-ylmethyl)-8-aza-bicyclo[3.2.1]octane-3-carboxylic Acid 2-Fluorobenzylamide In a similar manner to Step 6, Example 1, reductive alkylation of 8-aza-bicyclo[3.2.1]octane-3-carboxylic acid 2-fluoro-benzylamide was performed with 1-(2-trimethylsilylethoxymethyl)-1H-benzimidazole-2-carbaldehyde. After hydrolytic deprotection of the SEM protecting group, a mixture of exo and endo-8-(1H-benzimidazol-2-ylmethyl)-8-aza-bicyclo[3.2.1]octane-3-carboxylic acid 2-fluorobenzylamide was obtained. The exo and endo forms were separated by preparative TLC eluting with 90:10 chloroform:methanol.

The faster moving band was the endo isomer: MS (m+1)= 393.5; 1H NMR (400 MHz, CDCl$_3$) 7.7 (br s, 1H), 7.5 (br s, 1H), 7.4–7.0 (complex, 6H), 5.9 (br, 1H), 4.5 (d, 2H), 3.8 (s, 2H), 3.3 (s, 2H), 2. 5 (m, 1–1H), 2.1 (m, 4H), 1.6 (m, 3H).

The slower band was the exo isomer: MS (m+1)=393.5; $^1$H NMR (400 MHz, CDCl$_3$) 7.7 (br s, 2H), 7.4–7.0 (complex, 6H), 5.9 (br, 1H), 4.5 (d, 2H), 3.9 (s, 2H), 3.15 (s, 2H), 2.6 (m, 1H), 2.3 (m, 2H), 2.1 (d, 2H), 2.0 (m, 2H), 1.9 (m, 2H).

Example 22

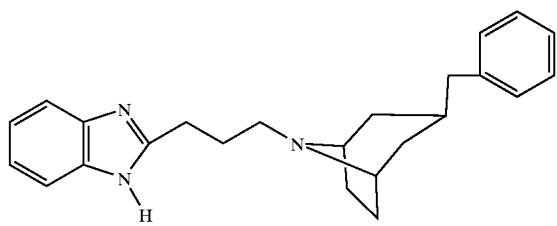

2-[3-(3-Benzyl-8-aza-bicyclo[3.2.1-]oct-8-yl)-propyl]-1H-benzimidazole

Example 22 was prepared by the following procedure.

Step 1:

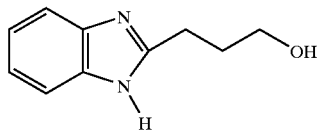

3-(1H-Benzimidazol-2-yl)-propan-1-ol

A mixture of 5.4 g of 1,2-phenylenediamine and 4.5 g of dihydro-furan-2-one in 50 mL of 4N hydrochloric acid was heated to reflux for 20 h, 1 teaspoon of decolorizing carbon added, and after another 15 min reflux, filtered hot. The filtrate was concentrated under reduced pressure to near dryness, the residue made basic (pH=8) with saturated sodium bicarbonate and extracted into 3×80 mL of ether. The combined extracts were dried over magnesium sulfate and concentrated under reduced pressure. After drying under vacuum, 8.4 g of 3-(1H-benzimidazol-2-yl)-propan-1-ol was obtained as a solid.

Step 2:

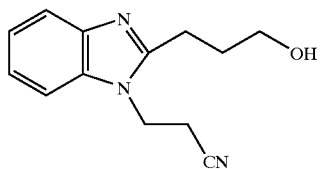

3-[2-(3-Hydroxy-propyl)-benzimidazol-1-yl]-propionitrile

To a stirred solution of 3.8 g of 3-(1H-benzimidazol-2-yl)-propan-1-ol and 4 g dihydropyran in 500 mL of THE was added p-toluenesulfonic acid monohydrate until the pH was about 3 (indicator paper). After stirring overnight, an additional 2 mL of dihydropyran was added: After 2 additional hours, the conversion was complete. The mixture was concentrated under reduced pressure and partitioned between 250 mL of 1N NaOH and 2×250 mL of ether. After drying over magnesium sulfate the combined extracts were concentrated to dryness. To a solution of the resulting crude oily 2-[3-(tetrahydro-pyran-2-yloxy)-propyl]-1H-benzimidazole (14 g) in 250 mL of acetonitrile was added 5 mL of acrylonitrile, 2 drops of 1M tetrabutylammonium fluoride in THF and 1 drop 10N NaOH. After heating to 85° C. for 16 h, conversion was complete (TLC elution with 90:10 methylene chloride:methanol). After concentration under reduced pressure, the residue was partitioned between 2×200 mL of ethyl acetate and 200 mL of water. The combined extracts were dried over magnesium sulfate and concentrated under reduced pressure. The crude 3-(2-[3-(tetrahydro-pyran-2-yloxy)-propyl]-benzimidazol-1-yl}-propionitrile was stirred in 250 mL of methanol with sufficient p-toluenesulfonic acid monohydrate to make the solution acidic (pH=1–2). After stirring overnight, the solution was concentrated under reduced pressure, made basic (pH=8) with 1N sodium hydroxide and extracted into 8×50 mL of ethyl acetate. The aqueous layer was saturated with NaCl to aid in extraction of the product. The combined extracts were dried over magnesium sulfate and concentrated under reduced pressure. Chromatography using a gradient of ethyl acetate, then 10% methanol in ethyl acetate, followed by trituration with ether-hexane gave 4.8 g of 3-[2-(3-hydroxy-propyl)-benzimidazol-1-yl]-propionitrile as a solid.

Step 3:

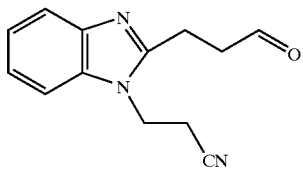

3-[2-(3-Oxo-propyl)-Benzimidazol-1-yl]-propionitrile

To a stirred solution of 0.5 g of oxalyl chloride in 15 mL of methylene chloride cooled to −78° C. was added 1 mL of anhydrous DMSO. After 15 min, a solution of 1 g of 3-[2-(3-hydroxy-propyl)-benzimidazol-1-yl]-propionitrile in 50 mL of methylene chloride and 10 mL of anhydrous DMSO was added while keeping the temperature below −50° C. There was considerable precipitate which redissolved on warming to 0° C. over 20 min. After cooling back down to −50° C., 5 mL of triethyl amine was added and the mixture allowed to warm to room temperature. After 15 min, the mixture was diluted with 250 mL of water, shaken and separated. The organic layer was dried over magnesium sulfate and concentrated under reduced pressure. The crude 3-[2-(3-oxo-propyl)-Benzimidazol-1-yl]-propionitrile was an amber resin (1 g), and contained only traces of the starting alcohol by TLC (90:10 methylene chloride:methanol).

Step 4:

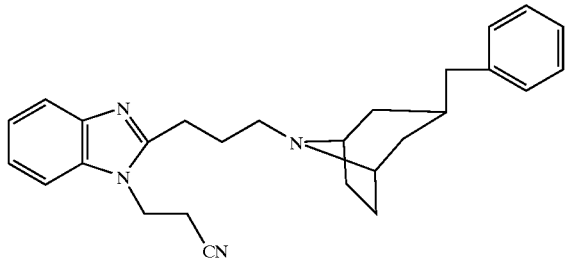

3-{2-[3-(3-Benzyl-8-aza-bicyclo[3.2.1]oct-8-yl)-propyl]-benzimidazol-1-yl}-propionitrile A mixture of 0.25 g of 3-benzyl-8-aza-bicyclo[3.2.1]octane, 0.4 g of 1-3-[2-(3-oxo-propyl)-Benzimidazol-1-yl-]-propionitrile, 5 mL of 1,2-dichloroethane and 0.3 g of sodium triacetoxyborohydride was stirred at room temperature for 24 h. The reaction mixture was diluted with 50 mL chloroform and 10 mL saturated aqueous $Na_2CO_3$ and the layers separated. The aqueous layer was extracted with 2×25 mL of chloroform and the combined organic layers dried over magnesium sulfate and concentrated under reduced pressure. Low pressure chromatography eluting with a gradient of 70:30 ethyl acetate:methanol to 70:30:5 ethyl acetate:methanol triethylamine gave 400 mg of pure 3-{2-[3-(3-benzyl-8-aza-bicyclo[3.2.1]oct-8-yl)-propyl-]-benzimdazol-1-yl-)-}-propionitrile as a gum.

Step 5:

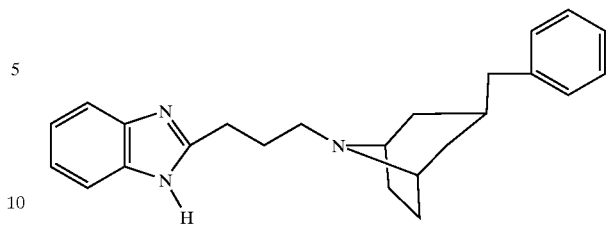

2-[3-(3-Benzyl-8-aza-bicyclo[3.2.1]oct-8-yl)-propyl]-1H-benzimidazole

A mixture of 0.4 g of 3-{2-[3-(3-benzyl-8-aza-bicyclo[3.2.1]oct-8-yl)-propyl]-benzimidazol-1-yl }-propionitrile, 20 mL of isopropanol and 2 mL of 0.4M sodium in isopiopanol was heated to reflux for 2 h. Conversion was complete by TLC (80:20:1 ethyl acetate:methanol:triethylamine). The mixture was cooled, diluted with 10 mL of saturated sodium bicarbonate and concentrated. The residue was partitioned between 3×100 mL of chloroform and 50 mL of water. After drying over magnesium sulfate and concentration under reduced pressure, the residue was purified by preparative TLC eluting with 400:100:25 ethyl acetate:methanol:triethylamine. The major band (UV visualization) was 2-[3-(3-benzyl-8-aza-bicyclo[3.2.1]oct-8-yl)-propyl]-1H-benzimidazole (258 mg): MS (m+1)=362.5; $^1$H NMR (400 MHz, CDCl$_3$) 7.58 (d, 1H), 7.52 (d, 1H), 7.6–7.2 (complex, 7H), 3.38 (s, 2H), 3.18 (m, 2H), 2.82 (m, 2H), 2.6 (m, 2H), 2.22 (m, 2H), 2.1 (m, 2H), 1.85 (m, 5H), 1.6 (m, 2H).

Example 23

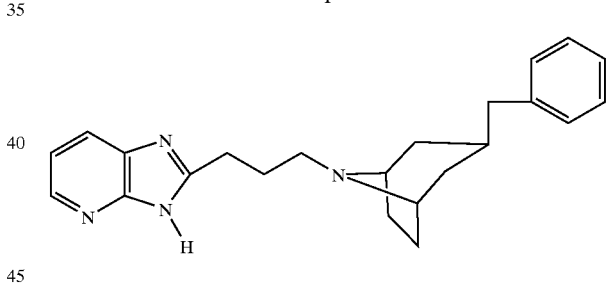

2-[3-(3-Benzyl-8-aza-bicyclo[3.2.1]oct-8-yl)-propyl]-3H-imidazo[4,5-b]pyridine

Example 23 was prepared by the following procedure.

Step 1:

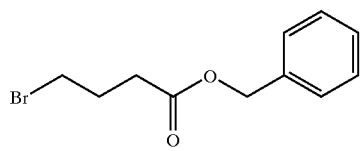

4-Bromo-butyric Acid Benzyl Ester

To an ice cold solution of 5 g of 4-bromobutyric acid and 5.5 g of benzylchloroformate in 100 mL of dichloromethane was added 5 mL of triethylamine and then 700 mg of 4-dimethylaminopyridine. A vigorous exothermic reaction ensued with evolution of carbon dioxide. After stirring for 3 h, the mixture was diluted with 100 mL of dichloromethane and washed with 200 mL of saturated sodium bicarbonate, dried over magnesium sulfate, and concentrated to an oil. Azeotropic drying with toluene gave 8 g of 4-bromobutyric acid benzyl ester as a clear oil.

Step 2:

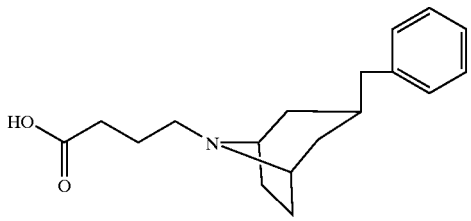

4-(3-Benzyl-8-aza-bicyclo[3.2.1]oct-8-yl)-butyric Acid

A mixture of 0.9 g of 4-bromobutyric acid benzyl ester, 0.5 g of 3-benzyl-8-aza-bicyclo[3.2.1]octane, 0.6 mL of N,N-diisopropylethylamine and 20 mL of acetonitrile was heated to 80° C. for 4 h. The mixture was cooled, concentrated under reduced pressure and partitioned between chloroform and saturated sodium carbonate. After drying over magnesium sulfate the extracts were concentrated to a thick oil, 1.4 g, which was a mixture of the benzyl ester of 4-(3-benzyl-8-aza-bicyclo[3.2.1]oct-8-yl)-butyric acid, benzyl 4-bromobutyrate, and butyrolactone. Hydrogenation over 0.5 g of palladium on carbon in 100 mL of ethanol under 1 atm of hydrogen overnight gave 0.9 g of 4-(3-benzyl-8-aza-bicyclo[3.2.1]oct-8-yl)-butyric acid after drying under vacuum at 100 ° C. overnight which was homogeneous by TLC (90:10:1 chloroform:methanol:ammonium hydroxide).

Step 4:

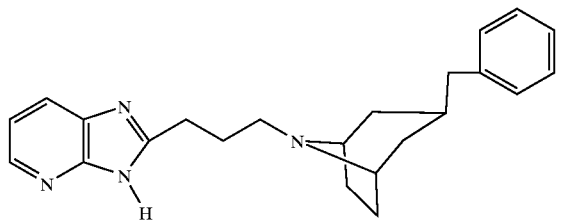

2-[3-(3-Benzyl-8-aza-bicyclo[3.2.1]oct-8-yl)-propyl]-3H-imidazo[4,5-b]pyridine

A mixture of 0.66 g of 4-(3-benzyl-8-aza-bicyclo[3.2.1]oct-8-yl)-butyric acid, 0.25 g of 1,2-diaminopyridine and 6 g of polyphosphoric acid was heated to 185° C. for 2 h. The mixture was cooled and stirred with 100 mL of 3N sodium hydroxide for 1 h after becoming homogeneous. The solution was extracted with 5×100 mL of chloroform and the combined extracts washed 3×50 mL of dilute ammonium hydroxide, heated with 1 g of decolorizing carbon for 10 min, cooled, filtered and concentrated. Purification of the residue by chromatography, eluting with 400:100:25 ethyl acetate:methanol:triethylamine gave 249 mg of 2-[3-(3-benzyl-8-aza-bicyclo[3.2.1]oct-8-yl)-propyl]-3H-imidazo[4,5-b]pyridine: MS (m+1)=363.5; $^1$H NMR (400 MHz, CDCl$_3$) 8.38 and 8.3 (2×d, 1H), 7.9 and 7.8 (2×d, 1H), 7.4–7.1 (complex, 6H), 3.42 (s, 2H), 3.22 (m, 2H), 2.82 (m, 2H), 2.75 (m, 2H), 2.4 (m, 2H), 2.2 (m, 1H), 2.0 (m, 5H), 1.6 (m, 2H).

Example 24

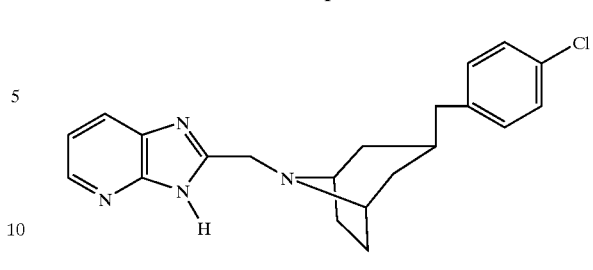

2-[3-(4-Chloro-benzyl)-8-aza-bicyclo [3.2.1]oct-8-ylmethyl-]-3H-imidazo[4,5-b]pyridine Example 24 was prepared in a similar manner to Example 1, Steps 1–6, but substituting 3H-imidazo[4,5-b]pyridine for benzimidazole in Step 2. Chromatography on a Chiralpak™ gave endo 2-[3-(4-chloro-benzyl)-8-aza-bicyclo[3.2.1]oct-8-ylmethyl]-1H-benzimidazole: RT=17.1 min; MS (m+1)= 367; $^1$H NMR (400 MHz, CDCl$_3$ 3.8 (s, 2H), 3.2 (s, 2H), 2.70 (d, 2H), 1.8 (d, 2H).

Later fractions gave exo 2-[3-(4-chloro-benzyl)-8-aza-bicyclo[3.2.1]oct-8-ylmethyl]-1H-benzimidazole: RT=9 min; MS (m+1)=367; $^1$H NMR (400 MHz, CDCl$_3$) 9.75 (br, 1H), 8.4 (d, 1H), 7.95 (d, 1H), 7.3–7.2 (m, 3H), 7.05 (d, 2H), 3.8 (s, 2H), 3.2 (s, 2H), 2.45 (d, 2H), 2.05 (d, 2H), 1.8 (m, 1H), 1.6 (d, 2H), 1.5 (m, 3H), 1.2 (m, 1H).

Example 25

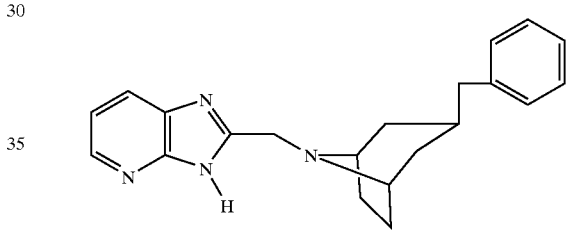

2-(3-Benzyl-8-aza-bicyclo[3.2.1]oct-8-ylmethyl)-3H-imidazo[4,5-b]pyridine

Example 25 was prepared in a similar manner to Example 24, but substituting 3-benzyl-8-aza-bicyclo[3.2.1]octane for 3-(4-chloro-benzyl)-8-aza-bicyclo[3.2.1]octane: MS (m+1)=333.5; $^1$H NMR (400 MHz, CDCl$_3$) 9.75 (br, 1H), 8.4 (d, 1H), 7.95 (d, 1H), 7.4–7.05 (m, 6H), 3.9 (s, 2H), 3.22 (s, 2H), 2.78 (d, 0.65×2H), 2.55 (d, 0.35×2H), 2.18 (m, 4H), 2.05 (m, 1H), 1.9 (m, 1H), 1.6 (d, 1H), 1.5 (d, 2H), 1.4 (d, 1H).

Example 26

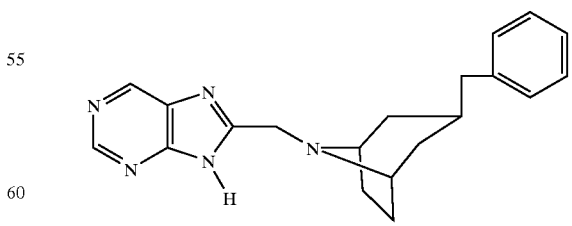

8-(3-Benzyl-8-aza-bicyclo[3.2.1]oct-8-ylmethyl)-9H-purine

Example 26 was prepared in a similar manner to Example 25, but substituting 9-(2-trimethylsilanyl-ethoxymethyl)-

9H-purine-8-carbaldehyde for 3-(2-trimethylsilanyl-ethoxymethyl)-3H-imidazo[4,5-b-]pyridine-2-carbaldehyde: MS (m+1)=335.5; $^1$H NMR (400 MHz, CDCl$_3$) 9.02 (s, 1H), 8.95 (s, 1H), 7.3–7.1 (m, 5H), 3.9 (s, 2H), 3.22 (s, 2H), 2.78 (d, 0.65×2H), 2.55 (d, 0.35×2H), 2.18 (m, 4H), 2.05 (m, 1H), 1.9 (m, 1H), 1.5 (m, 1H), 1.5 (d, 2H), 1.4 (d, 1H).

Example 27

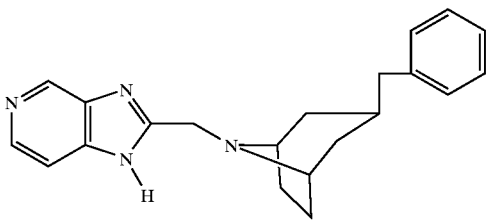

2-(3-Benzyl-8-aza-bicyclo[3.2.1]oct-8-ylmethyl)-1H-imidazo[4,5-c]pyridine

Example 27 was prepared in a similar manner to Example 25, but substituting 1-(2-trimethylsilanyl-ethoxymethyl)-1H-imidazo[4,5-c-]pyridine-2-carbaldehyde for 3-(2-trimethylsilanyl-ethoxymethyl)-3H-imidazo[4,5-b]pyridine-2-carbaldehyde: MS (m+1)=335.5; $^1$H NMR (400 MHz, CDCl$_3$) 9.02 (s, 1H), 8.4 (m, 1H), 7.5 (s, 1H), 7.3–7.1 (m, 5H), 3.9 (s, 2H), 3.22 (s, 2H), 2.78 (d, 0.65×2H), 2.55 (d, 0.35×2H), 2.18 (m, 4H), 2.05 (m, 1H), 1.9 (m, 1H), 1.65 (d, 1H), 1.5 (m, 2H), 1.4 (d, 1H).

Example 28

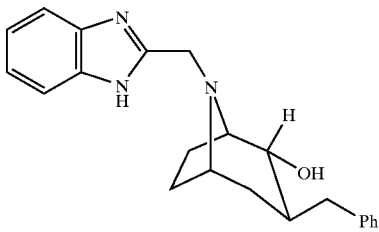

(+)8-(1H-Benzimidazol-2-ylmethyl)-3-exo-benzyl-8-aza-bicyclo[3.2.1]octan-2-endo-ol and (−)8-(1H-Benzimidazol-2-ylmethyl)-3-exo-benzyl-8-aza-bicyclo[3.2.1]octan-2-endo-ol Example 28 was prepared by the following procedure.
Step 1:

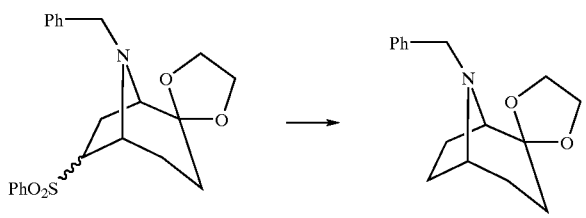

(±)-8-Benzyl-8-aza-bicyclo[3.2.1]octan-2-one Ethylene Acetal

The procedure described in *Synth. Commun.*, 25:3681–3690 (1995) to prepare the analogous 8-methyl compounds was used. In a three-neck flask equipped with a thermometer, an argon inlet, and a powder funnel were placed sodium hydrogenphosphate (dibasic) (7.10g, 50.0 mmol), and dry methanol (8 mL). A solution of (±)-6-benzenesulfonyl-8-benzyl-8-aza-bicyclo[3.2.1]octan-2-one ethylene acetal (*J. Heterocyclic Chem.*, 34:1139–1146 (1997) (2.00 g, 5.0 mmol) in tetrahydrofuran (16 mL) was added. Sodium mercury amalgam (20% sodium) (5 g) was added portionwise with stirring at such a rate as to keep the temperature below 50° C. The mixture was stirred an additional 1.5 h at ambient temperature. The organic solution was decanted away from the inorganic residue. The inorganic residue was washed with tetrahydrofuran (3×8 mL). The combined organic portion was concentrated under reduced pressure. The residue was dissolved in water (32 mL) and extracted with dichloromethane (4×16 mL). The combined extract was washed with brine (20 mL), dried (sodium sulfate), filtered, and the solvent was evaporated under reduced pressure to give crude product (1.21 g, 89%) as an oil.

$^1$H NMR (CDCl$_3$) 7.44 (2H, d, J 7.5 Hz), 7.4 (3H, m), 3.9 (3H, m), 3.77 (1H, m), 3.65 (1H, d, J 14 Hz), 3.53 (1H, d, J 14 Hz), 3.19 (1H, m), 2.95 (1H, d, J 7 Hz), 2.03–1.85 (3H, m), 1.75 (1H, m), 1.65 (1H, m), 1.59 (2H, m), 1.41 (1H, m).

Step 2:

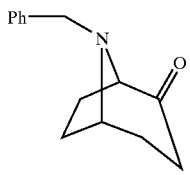

(±)-8-Benzyl-8-aza-bicyclo[3.2.1]octan-2-one

The procedure described in *Synth. Commun.*, 25:3681–3690 (1995) to prepare the analogous 8-methyl compounds was used. This intermediate product has been described in Blarney and Markwell, EP 76089 A2 830406. Further, the (+)- and (−)-enantiomers were described in *J. Org. Chem.*, 63:4069–4078(1998).

A solution of (±)-8-benzyl-8-aza-bicyclo[3.2.1]octan-2-one ethylene acetal (9.47 g, 36.5 mmol) in 3N perchloric acid (243 mL, 20 equiv.) was stirred at 90° C. for 18 h. The solution was cooled to ambient temperature and poured into ice-cold 3N sodium hydroxide solution (250 mL). The mixture was extracted with dichloromethane (3×175 mL). The combined extract was washed with brine (100 mL), dried (sodium sulfate), filtered, and the solvent was evaporated under reduced pressure to give crude product (8.23 g).

The crude product was dissolved in dichloromethane (200 mL), di-tert-butyl dicarbonate (3.24 mL, 15.0 mmol) was added, and the solution was stirred at ambient temperature for 18 h. The solution was concentrated under reduced pressure and the residue was purified by flash column chromatography on silica gel, eluting with ethyl acetate/hexane (20:80 increasing to 50:50).

The first compound to elute was (±)-benzyl-(7-oxo-cyclohept-3-enyl)-carbamic acid tert-butyl ester (1.00 g, 9%), followed by product (±)-8-benzyl-8-aza-bicyclo[3.2.1] octan-2-one (2.88 g, 37%) as a pale yellow oil, followed by mixed product/recovered (±)-8-benzyl-8-aza-bicyclo[3.2.1-]octan-2-one. ethylene acetal (3.31 g). The mixed product/recovered starting material was recycled in 3N perchioric acid (30 mL) to afford additional product (2.77 g, 35%).

¹H NMR (CDCl₃) 7.33 (4H, m), 7.25 (1H, m), 3.68 (2H, s), 3.36 (2H, d, J 6 Hz), 2.42–2.30 (2H, m), 2.20 (4H, m), 1.75 (2H, m).

Step 3:

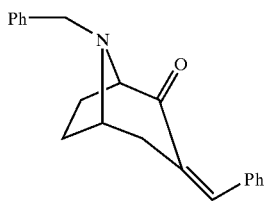

(±)-8-Benzyl-3-benzylidene-8-aza-bicyclo[3.2.1] octan-2-one

A 5N sodium hydroxide solution (1.62 mL, 0.5 equiv.) was added to (±)-8-benzyl-8-aza-bicyclo[3.2.1]octan-2-one (3.49 g, 16.2 mmol), followed by a solution of benzaldehyde (2.59 mL, 2.69 g, 16.2 mmol) in ethanol (160 mL). The solution was stirred at ambient temperature for 4.5 h. The solution was concentrated under reduced pressure, and the residue was taken up in dichloromethane (160 mL). The mixture was washed with water (160 mL) and brine (160 mL), dried (sodium sulfate), filtered, and the solvent evaporated under reduced pressure to give crude product (4.96 g, theoretical yield 4.92 g) as an orange oil.

¹H NMR (CDCl₃) 7.64 (1H, s), 7.47 (2H, d, J 14 Hz), 7.41–7.24 (8H, m), 3.77 (2H, s), 3.66 (1H, d, J 7.5 Hz), 3.53 (1H, t, J 6 Hz), 3.18 (1H, m), 2.66 (1H, d, J 17 Hz), 2.31 (1H, m), 2.18 (1H, m), 1.79 (1H, m), 1.59 (1H, m).

Step 4:

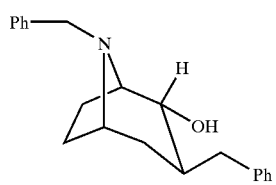

(±)-3-exo-Benzyl-8-benzyl-8-aza-bicyclo[3.2.1] octan-2-endo-ol

A mixture of crude (±)-8-benzyl-3-benzylidene-8-aza-bicyclo[3.2.1]octan-2-one (4.95 g, 16.2 mmol) and platinum (IV) oxide (0.30 g) in methanol (80 mL) was hydrogenated on a Parr hydrogenation apparatus (51 psi) for 42 h. The catalyst was removed by filtration through Celite®. The filter cake was washed with methanol (3×40 mL) and the filtrate was concentrated under reduced pressure to give a yellow gum (4.98 g). The gum was purified by flash column chromatography on silica gel, eluting with ethyl acetate/hexane (25:75 increasing to 67:33). The first compound to elute was the epimeric byproduct (±)-3-exo-benzyl-8-benzyl-8-aza-bicyclo[3.2.1]octan-2-exo-ol (0.34 g, 7%),as an oil, followed by the partial reduction byproduct (±)-8-benzyl-3-benzylidene-8-aza-bicyclo[3.2.1]octan-2-endo-ol (1.14 g, 23%),as an oil, followed by the product (1.98 g, 40%), as a white solid, m.p. 104–105° C.

¹H NMR (CDCl₃) 7.37–7.25 (7H, m), 7.19 (3H, m), 3.57 (1H, m), 3.52 (2H, d, J 6 Hz), 3.09 (3H, m), 2.36 (1H, m), 1.98 (1H, m), 1.83 (2H, m), 1.58 (1H, m), 1.45 (4H, m). Mass spec.: 308.4 (M+1).

Step 5:

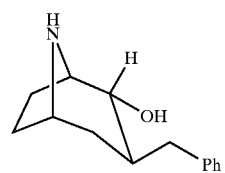

(±)-3-exo-Benzyl-8-aza-bicyclo[3.2.1]octan-2-endo-ol

A mixture of (±)-3-exo-benzyl-8-benzyl-8-aza-bicyclo [3.2.1]octan-2-endo-ol (1.97 g, 6.4 mmol) and 10% palladium on carbon (0.60 g) in methanol (80 mL) was hydrogenated on a Parr hydrogenation apparatus (51 psi) for 18 h. The catalyst was removed by filtration through Celite®. The filter cake was washed with methanol (3×40 mL) and the filtrate was concentrated under reduced pressure to give crude product (1.39 g). The crude product was dissolved in dichloromethane and filtered through a pad of silica gel eluting with methanol:dichloromethane:concentrated ammonium hydroxide (20:80:2). The filtrate was concentrated under reduced pressure to give product (1.36 g, 98%) as a solid white foam.

¹H NMR (CDCl₃) 7.28 (2H, m), 7.18(3H, m), 3.40 (3H, m), 3.09 (1H, dd, J 13, 4 Hz), 2.37 (1H, m), 1.91 (2H, m), 1.88–1.61 (4H, m), 1.42 (2H, m), 1.30 (1H, m). Mass spec.: 218.2 (M+1).

Step 6:

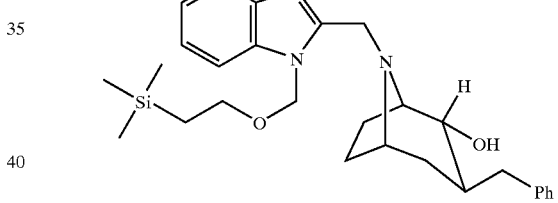

(±)-3-exo Benzyl-8-[1-(2-trimethylsilanyl-ethoxymethyl)-1H-benzimidazol-2-ylmethyl]-8-aza-bicyclo[3.2.1]octan-2-endo-ol To a mixture of (±)-3-exo-benzyl-8-aza-bicyclo[3.2.1] octan-2-endo-ol (1.35 g, 6.2 mmol) in dichloromethane (6 mL) under an atmosphere of argon was added a solution of 1-(2-trimethylsilanyl-ethoxymethyl)-1H-benzimidazol-2-carbaldehyde (2.05 g, 7.4 mmol) in dichloromethane (6 mL). The mixture was stirred 15 minutes and sodium triacetoxyborohydride (1.57 g, 7.4 mmol) was added. The mixture was stirred 62 h at ambient temperature. The mixture was diluted with ethyl acetate (75 mL), washed with saturated sodium bicarbonate solution (2×35 mL), water (35 mL), and brine (35 mL). The organic solution was dried (sodium sulfate), filtered, and the solvent evaporated under reduced pressure to give crude product (3.07 g) as an orange solid. The crude product was purified by flash column chromatography on silica gel, eluting with ethyl acetate/hexane (50:50) increasing to ethyl acetate (100%) to give product (1.75 g, 59%) as a pale yellow solid.

¹H NMR (CDCl₃) 7.76 (1H, dd, J 6.5, 2 Hz), 7.52 (1H, dd, J 6.5, 2 Hz), 7.30 (4H, m), 7.20 (3H, m), 5.85 (2H, dd, J 19, 11 Hz), 3.90 (2H, d, J 2 Hz), 3.59 (2H, t, J, 8 Hz), 3.53 (1H, m), 3.18 (2H, m), 3.10 (1H, dd, J 13, 4 Hz), 2.36 (1H, dd, J 13, 9 Hz), 2.10 (1H, m), 1.98 (1H, m), 1.91 (1H, m), 1.63 (2H, m), 1.51 (1H, d, J 5 Hz), 1.46 (1H, m), 1.38 (1H, m), 0.95 (2H, t, J, 8 Hz), 0.04 (9H, s).

Step 7:

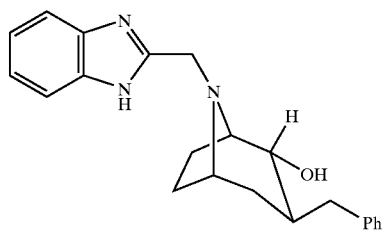

(±)8-(1H-Benzimidazol-2-ylmethyl)-3-exo-benzyl-8-aza-bicyclo[3.2.1]octan-2-endo-ol To a suspension of (±)-3-exo Benzyl-8-[1-(2-trimethylsilanyl-ethoxymethyl)-1H-benzimidazol-2-ylmethyl]-8-aza-bicyclo[3.2.1]octan-2-endo-ol (1.74 g, 3.65 mmol) in ethanol (24 mL) was added 3N hydrochloric acid (3 ml, 2.5 equiv.). The mixture was stirred for 6 h at 80° C. The cooled solution was concentrated under reduced pressure. The residue was taken up in ethyl acetate (250 mL), washed with saturated sodium bicarbonate solution (2×100 mL), water (100 mL), and brine (100 mL). The organic solution was dried (sodium sulfate), filtered, and the solvent evaporated under reduced pressure to give crude product (1.23 g, 100%) as a yellow solid. A portion (60 mg) of the crude product was chromatographed on a silica gel prep plate (1 mm), eluting with methanol:dichloromethane:concentrated ammonium hydroxide (10:90:1) to give a yellow solid (40 mg). The solid was triturated with ethyl acetate, filtered off, and dried in vacuo to give product (32 mg) as a white solid, m.p. 218–219° C.

$^1$H NMR (CDCl$_3$) 9.63 (1H,br, s), 7.70 (1H, dd, J 6, 2 Hz), 7.50 (1H, dd, J 6, 2 Hz), 7.31–7.18 (7H, m), 3.82 (2H, d, J 1 Hz), 3.62 (1H, d, J, 10 Hz), 3.12 (3H, m), 2.42 (1H, dd, J 13,9 Hz), 2.01 (1H, m), 1.91 (2H, m), 1.65 (2H, m), 1.48 (1H, m), 1.41 (2H, m). Analysis calculated for C$_{22}$H$_{25}$N$_3$O C, 76.05; H, 7.25; N, 12.09. Found; C, 76.15; H, 6.98; N, 12.09.

(+)8-(1H-Benzimidazol-2-ylmethyl)-3-exo-benzyl-8-aza-bicyclo[3.2.1]octan-2-endo-ol and (−)8-(1H-Benzimidazol-2-ylmethyl)-3-exo-benzyl-8-aza-bicyclo[3.2.1-]octan-2-endo-ol Crude (±)8-(1H-benzimidazol-2-ylmethyl)-3-exo-benzyl-8-aza-bicyclo[3.2.1]octan-2-endo-ol (1.23 g) was resolved by preparative chiral HPLC (three runs, Chiralcel™ OD column, 5×50 cm, hexane:isopropanol:diethylamine 80:20:0.1, 60 mL/min at 210 nm.

The first enantiomer to elute was (−)8-(1H-benzimidazol-2-ylmethyl)-3-exo-benzyl-8-aza-bicyclo[3.2.1]octan-2-endo-ol (0.65 g) as a solid white foam, RT=18.9 min. The dihydrochloride salt melted at 234–236° C.

Mass spec.: 348.4 (M+1). [□]$_D$ −92.2° (c 0.500, methanol). Analysis calculated for C$_{22}$H$_{25}$N$_3$O.2 HCl C, 62.86; H, 6.47; N, 10.00. Found: C, 62.54; H, 6.29; N, 9.89.

The second enantiomer to elute was (+)8-(1H-benzimidazol-2-ylmethyl)-3-exo-benzyl-8-aza-bicyclo[3.2.1]octan-2-endo-ol (0.58 g) as a solid white foam, RT=34.0 min. The dihydrochloride salt melted at 234–236° C.

Mass spec.: 348.4 (M+1). [□]$_D$ +95.0° (c 0.545, methanol). Analysis calculated for C$_{22}$H$_{25}$N$_3$O.2 HCl (.0.05 ethanol.0.40 water) C, 61.74; H, 6.49; N, 9.78. Found: C, 61.75; H, 6.23; N, 9.71.

Example 29

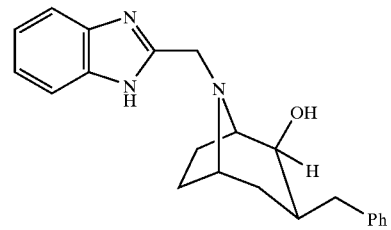

(+)8-(1-Benzimidazol-2-ylmethyl)-3-exo-benzyl-8-aza-bicyclo[3.2.1-]octan-2-exo-ol and (−)8-(1H-Benzimidazol-2-ylmethyl)-3-exo-benzyl-8-aza-bicyclo[3.2.1]octan-2-exo-ol Example 29 was prepared by the following procedure.

Step 1:

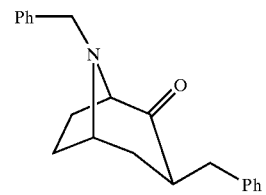

(±)-3-exo-Benzyl-8-benzyl-8-aza-bicyclo[3.2.1]octan-2-one

A mixture of crude (±)-8-benzyl-3-benzylidene-8-aza-bicyclo[3.2.1]octan-2-one (7.08 g, 22 mmol) and 10% palladium on carbon (0.75 g) in methanol (200 mL) was hydrogenated (1 atm) for 18 hours. The catalyst was removed by filtration through Celite. The filter cake was washed with methanol (3×75 mL) and the filtrate was concentrated under reduced pressure to give crude product (6.10 g, 91%), as a yellow oil.

An aliquot of product (100 mg) was-chromatographed on a 2 mm silica prep plate eluting with ethyl acetate:hexane (20:80) to give purified product (61 mg) as a pale amber oil.

$^1$H NMR (CDCl$_3$) 7.28 (7H, m), 7.18 (3H, m), 3.61 (2H, s), 3.42 (1H, d, J 7 Hz), 3.32 (2H, m), 2.61 (1H, m), 2.51 (1H, m), 2.17 (2H, m), 1.87–1.67 (4H, m). Mass spec.: 306.4 (M+1).

Step 2:

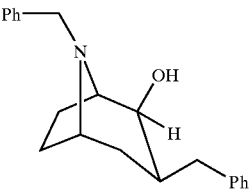

(±)-3-exo-Benzyl-8-benzyl-8-aza-bicyclo[3.2.1]octan-2-exo-ol

To a solution of (±)-3-exo-benzyl-8-benzyl-8-aza-bicyclo[3.2.1]octan-2-one (3.05 g, 10.0 mmol) in dry toluene (150 mL) cooled to −50° C. (dry ice/chloroform bath) was added dropwise over six minutes a solution of diisobutylaluminum hydride in toluene (1.5M, 23.3 mL, 3.5 equiv.). The solution was stirred one hour at −50° C. To the solution were added dropwise water (4 mL), 3N sodium hydroxide solution (4 mL), and water (12 mL). The mixture was dried (magnesium sulfate), filtered, and the solvent evaporated under reduced pressure to give crude product (2.50 g, 81%) as a yellow oil. The crude product was purified by flash column chromatography on silica gel, eluting with ethyl acetate/hexane (25:75) increasing to ethyl acetate (100%).

The first compound to elute was product (1.375 g, 45%), as an oil, followed by the epimeric byproduct (±)-3-exo-benzyl-8-benzyl-8-aza-bicyclo[3.2.1]octan-2-endo-ol (0.38 g, 12%), as a white solid.

$^1$H NMR (CDCl$_3$) 7.36 (4H, m), 7.27 (4H, m), 7.20 (2H, m), 3.45 (2H, dd, J 12, 21 Hz), 3.27 (1H, m), 3.21 (1H, d, J 5 Hz), 3.11 (1H, d, J 3 Hz), 2.75 (1H, dd, J 12, 8 Hz), 2.47 (1H, dd, J 13, 7 Hz), 1.97 (2H, m), 1.70 (1H, m), 1.52 (4H, m), 1.30 (1H, m). Mass spec.: 308.4 (M+1).

Step 3:

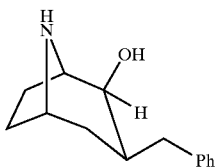

(±)-3-exo-Benzyl-8-aza-bicyclo[3.2.1]octan-2-exo-ol

A mixture of (±)-3-exo-benzyl-8-benzyl-8-aza-bicyclo[3.2.1]octan-2-exo-ol (2.80 g, 9.1 mmol) and 10% palladium on carbon (0.85 g) in methanol (75 mL) was hydrogenated on a Parr hydrogenation apparatus (52 psi) for 18 h. The catalyst was removed by filtration through Celite®. The filter cake was washed with methanol (3×40 mL) and the filtrate-was-concentrated under reduced pressure to give crude product (2.17 g). The crude product was purified by flash column chromatography on silica gel, eluting first with ethyl acetate/hexane (50:50) to remove impurities, then eluting with methanol:dichloromethane:concentrated ammonium hydroxide (20:80:2) to give product (1.81 g, 92%), as a pale yellow oil that crystallized on standing, m.p. 92–94° C.

$^1$H NMR (CDCl$_3$) 7.28 (2H, m), 7.20(3H, m), 3.42 (2H, m), 3.30 (1H, t, J 3 Hz), 2.74 (1H, dd, J 13, 8 Hz), 2.47 (1H, dd, J 13, 7 Hz), 2.2–1.8 (1H, br s), 1.75–1.61 (5H, m), 1.51 (2H, m), 1.30 (1H, m). Mass spec.: 218.2 (M+1).

Step 4:

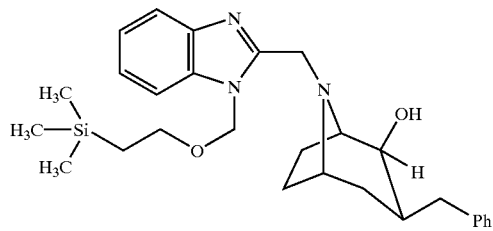

(±)-3-exo Benzyl-8-[1-(2-trimethylsilanyl-ethoxymethyl)-1H-benzimidazol-2-ylmethyl-]-8-aza-bicyclo[3.2.1]octan-2-exo-ol To a solution of (±)-3-exo-benzyl-8-aza-bicyclo[3.2.1]octan-2-exo-ol (1.52 g, 7.0 mmol) in dichloromethane (4 mL) under an atmosphere of argon was added 1-(trimethylsilyl)imidazole (1.10 mL, 1.05 g, 7.5 mmol). The solution was stirred two hours at ambient temperature. The solvent was evaporated under reduced pressure to give crude (±)-3-exo-benzyl-2-(exo-trimethyl-silanyloxy) 8-aza-bicyclo[3.2.1]octane (2.60 g) as an orange oil. Employing the procedure substantially as described above for (±)-3-exo benzyl-8-[1-(2-trimethylsilanyl-ethoxymethyl)-1H-benzimidazol-2-ylmethyl]-8-aza-bicyclo[3.2.1]octan-2-endo-ol, but substituting crude (±)-3-exo-benzyl-2-(exo-trimethyl-silanyloxy) 8-aza-bicyclo[3.2.1]octane (2.60 g, 7 mmol) for (±)-3-exo-benzyl-8-aza-bicyclo[3.2.1]octan-2-endo-ol, the product (2.36 g, 71%) was obtained as an orange gum.

$^1$H NMR (CDCl$_3$) 7.76 (1H, dd, J 7, 2 Hz), 7.50 (1H, dd, J 7, 2 Hz), 7.29 (4H, m), 7.21 (3H, m), 5.72 (2H, s), 3.83 (2H, dd, J 14, 13 Hz), 3.73 (2H, t, J, 8 Hz), 3.60 (1H, m), 3.31 (3H, m), 2.77 (1H, dd, J 13, 8 Hz), 2.48 (1H, dd, J 13, 7 Hz), 2.11 (2H, m), 1.74 (1H, m), 1.66–1.45 (2H, m), 1.32 (2H, m), 1.08 (2H, t, J, 8 Hz), 0.05 (9H, s).

Step 5:

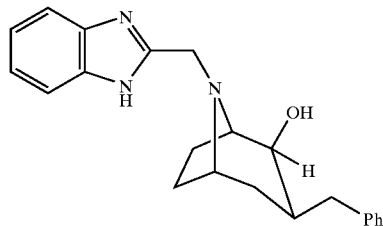

(±)8-(1H-Benzimidazol-2-ylmethyl)-3-exo-benzyl-8-aza-bicyclo[3.2.1]octan-2-exo-ol Employing the procedure substantially as described above for (±)8-(1H-benzimidazol-2-ylmethyl)-3-exo-benzyl-8-aza-bicyclo[3.2.1]octan-2-endo-ol, but substituting (±)-3-exo benzyl-8-[1-(2-trimethylsilanyl-ethoxymethyl)-1H-benzimidazol-2-ylmethyl]-8-aza-bicyclo[3.2.1]octan-2-exo-ol (2.34 g, 4.9 mmol) for (±)-3-exo benzyl-8-[1-(2-trimethylsilanyl-ethoxymethyl)-1H-benzimidazol-2-ylmethyl]-8-aza-bicyclo[3.2.1]octan-2-endo-ol, the product (1.34 g, 79%) was obtained as a solid yellow foam. A portion (149 mg) of the crude product was chromatographed on a silica gel prep plate (1 mm), eluting with methanol:dichloromethane:concentrated ammonium hydroxide (10:90:1) to give a yellow solid (107 mg). The solid was triturated with ethyl acetate, filtered off, and dried in vacuo to give product (79 mg) as a white solid, m.p. 208–209° C.

$^1$H NMR (CDCl$_3$) 10.16 (1H, br, s), 7.71 (1H, br s), 7.42 (1H, br s), 7.25 (4H, m), 7.18 (3H, m), 3.81 (2H, dd, J 30, 15 Hz), 3.43 (1H, s), 3.32 (1H, m), 3.20 (1H, d, J 3 Hz), 2.77 (1H, dd, J 13, 8 Hz), 2.51 (1H, dd, J 13, 7 Hz), 2.03 (2H, m), 1.81 (1H, m), 1.72–1.49 (4H, m), 1.40 (1H, m). Mass spec.: 348.4 (M+1). Analysis calculated for $C_{22}H_{25}N_3O$ (·0.05 ethyl acetate·0.25 water) C, 74.82; H, 7.26; N, 11.70. Found: C, 74.73; H, 6.99; N, 11.89.

Example 30

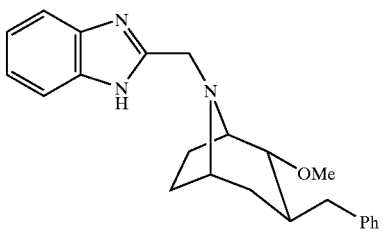

(±)-2-(3-exo-Benzyl-2-endo-methoxy-8-aza-bicyclo [3.2.1]oct-8-ylmethyl)-1H-benzimidazole Example 30 was prepared by the following procedure.
Step 1:

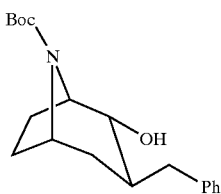

(±)-3-exo-Benzyl-2-endo-hydroxy-8-aza-bicyclo [3.2.1]octane-8-carboxylic Acid tert-Butyl Ester To a solution of (±)-3-exo-benzyl-8-aza-bicyclo[3.2.1] octan-2-endo-ol (240 mg, 1.1 mmol) in dichloromethane (5 mL) under an atmosphere of argon was added di-tert-butyl dicarbonate 0.276 mL. 262 mg, 1.2 mmol). The solution was stirred 18 hours at ambient temperature. The solution was diluted with dichloromethane (10 mL), washed with water (5 mL), and brine (5 mL), dried (sodium sulfate), filtered, and the solvent evaporated under reduced pressure to give crude product (384 mg, theoretical yield 349 mg) as a colorless oil.

Mass spec.: 318, 218.2 (M+1).
Step 2:

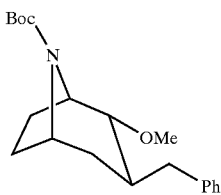

(±)-3-exo-Benzyl-2-endo-methoxy-8-aza-bicyclo [3.2.1]octane-8-carboxylic Acid tert-Butyl Ester Potassium hydride (25% in mineral oil) was placed in a round-bottom flask under a stream of argon and washed with hexane to remove mineral oil. The washed potassium hydride was suspended in dry tetrahydrofuran (2 mL). The mixture was cooled in an ice-bath and methyl iodide (0.081 mL, 185 mg, 1.3 mmol) was added. A solution of crude (±)-3-exo-benzyl-2-endo-hydroxy-8-aza-bicyclo[3.2.1] octane-8-carboxylic acid tert-butyl ester (382 mg, 1.1 mmol) in dry tetrahydrofuran (2 mL) was added dropwise over five minutes. The mixture was stirred with cooling for 15 minutes, then at ambient temperature for one hour. Saturated sodium bicarbonate solution (3 mL) was added dropwise, and the mixture was extracted with ethyl acetate (3×15 mL). The combined extract was washed with water (5 mL) and brine (5 mL), dried (sodium sulfate), filtered, and the solvent was evaporated under reduced pressure to give crude product (350 mg, 96%) as an oil. The crude product was purified by flash column chromatography on silica gel, eluting with ethyl acetate/hexane (25:75) to give product (247 mg, 68%) as a pale yellow oil: $^1$H NMR (CDCl$_3$) 7.26 (2H, m), 7.14(3H, m), 4.55–4.05 (3H, m), 3.44 (3H, s), 3.15–2.94 (2H, m), 2.29 (1H, m), 1.99–1.76 (4H, m), 1.58–1.24 (1H, m).

Step 3:

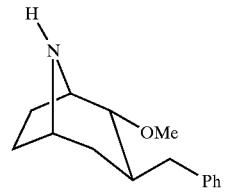

(±)-3-exo-Benzyl-2-endo-methoxy-8-aza-bicyclo [3.2.1]octane

A mixture of (±)-3-exo-benzyl-2-endo-methoxy-8-aza-bicyclo[3.2.1]octane-8-carboxylic acid tert-butyl ester (245 mg, 0.74 mmol), dioxane (1.5 mL), and 3N hydrochloric acid (1.0 mL, 4 equiv.) was heated at reflux for 3.5 h. The cooled mixture was made basic with saturated sodium carbonate solution and extracted with dichloromethane (3×10 mL). The combined extract was washed with brine (5 mL), dried (sodium sulfate), filtered, and the solvent was evaporated under reduced pressure to give crude product (155 mg, 91%) as a yellow oil.

Mass spec.: 232.3 (M+1). $^1$H NMR (CDCl$_3$) 3.42 (3H, s, —OCH$_3$).

Step 4:

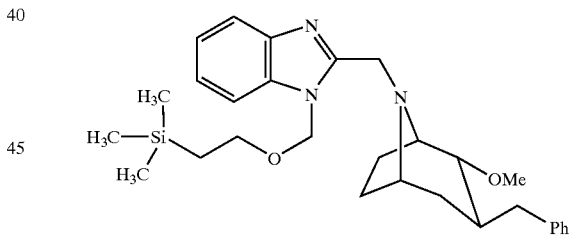

(±)-2-(3-exo-Benzyl-2-endo-methoxy-8-aza-bicyclo [3.2.1]oct-8-ylmethyl)-1-(2-trimethylsilanyl-ethoxymethyl)-1H-benzimidazole Employing the procedure substantially as described above for (±)-3-exo benzyl-8-[1-(2-trimethylsilanyl-ethoxymethyl)-1H-benzimidazol-2-ylmethyl]-8-aza-bicyclo [3.2.1]octan-2-endo-ol, but substituting (±)-3-exo-benzyl-2-endo-methoxy-8-aza-bicyclo[3.2.1-]octane for (±)-3-exo-benzyl-8-aza-bicyclo[3.2.1]octan-2-endo-ol $^1$H NMR (CDCl$_3$) 7.76 (1H, dd, J 7, 1 Hz), 7.52 (1H, dd, J 7, 2 Hz), 7.28 (4H, m), 7.18 (3H, m), 5.86 (2H, dd, J 31, 11 Hz), 3.90 (2H, s), 3.60 (2H, t, J, 8 Hz), 3.45 (1H, m), 3.36 (3H, d, J 1 Hz), 3.15 (2H, m), 2.99 (1H, dd, J 10, 3.5 Hz), 2.23 (1H, dd, J 13, 10 Hz), 2.08 (1H, m), 1.92 (2H, m), 1.62 (1H, m), 1.43 (1H, m), 1.29 (2H, m), 0.95 (2H, t, J, 8 Hz), 0.03 (9H, s).

Step 5:

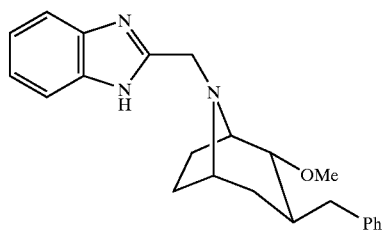

(±)-2-(3-exo-Benzyl-2-endo-methoxy-8-aza-bicyclo
[3.2.1]oct-8-ylmethyl)-1-H-benzimidazole Following the procedure substantially as described in Step 7, Example 28 above, the product precipitated from the reaction mixture as the dihydrochloride salt, m.p. 222–226° C.

$^1$H NMR (DMSO-d$_6$) 7.70 (2H, dd, J 6, 3 Hz), 7.34 (2H, dd, J 6, 3 Hz), 7.28 (2H, m), 7.18 (3H, m), 4.48 (2H, m), 4.36 (1H, br s), 4.00 (1H, br s), 3.50 (1H, d, J 10 Hz), 3.36 (3H, s), 3.03 (1H, dd, J 13, 3 Hz), 2.34 (1H, m), 2.27 (1H, m), 2.08 (3H, m), 1.84 (1H, m), 1.72 (2H, m), 1.43 (1H, d, J 13.5 Hz). Mass spec.: 362.4 (M+1). Analysis calculated for C$_{23}$H$_{27}$N$_3$O.2 HCl C, 63.59; H, 6.73; N, 9.67. Found: C, 63.57; H, 6.53; N, 9.74.

Example 31

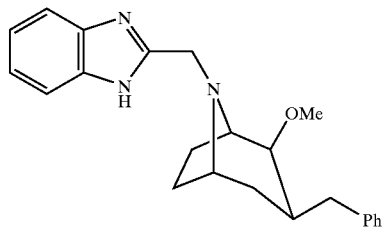

(±)-2-(3-exo-Benzyl-2-exo-methoxy-8-aza-bicyclo
[3.2.1]oct-8-ylmethyl)-1H-benzimidazole Example 31 was prepared by the following procedure.
Step 1:

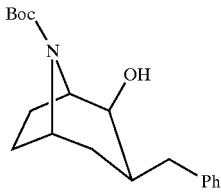

(±)-3-exo-Benzyl-2-exo-hydroxy-8-aza-bicyclo-
[3.2.1]octane-8-carboxylic Acid tert-Butyl Ester Employing the procedure substantially as described above for Example 30, but substituting (±)-3-exo-benzyl-8-aza-bicyclo[3.2.1]octan-2-exo-ol (240 mg, 1.1 mmol) for (±)-3-exo-benzyl-8-aza-bicyclo[3.2.1]octan-2-endo-ol, the product (389 mg, theoretical yield 349 mg) was obtained as a colorless oil.

Mass spec.: 318.2, 218.2 (M+1).

Step 2:

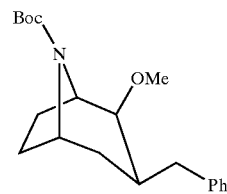

(±)-3-exo-Benzyl-2-exo-methoxy-8-aza-bicyclo
[3.2.1]octane-8-carboxylic Acid tert-Butyl Ester Employing the procedure substantially as described above, but substituting (±)-3-exo-benzyl-2-exo-hydroxy-8-aza-bicyclo[3.2.1]octane-8-carboxylic acid tert-butyl ester (387 mg, 1.1 mmol) for (±)-3-exo-benzyl-2-endo-hydroxy-8-aza-bicyclo[3.2.1]octane-8-carboxylic acid tert-butyl ester, the product (272 mg, 75%) was obtained as a pale yellow oil: $^1$H NMR (CDCl$_3$) 7.26 (2H, m), 7.17 (3H, m), 4.62–4.10 (3H, m), 3.36 (3H, d, J 16 Hz), 2.81–2.65 (2H, m).

Step 3:

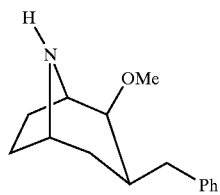

(±)-3-exo-Benzyl-2-exo-methoxy-8-aza-bicyclo
[3.2.1]octane

Employing the procedure substantially as described above, but substituting (±)-3-exo-benzyl-2-exo-methoxy-8-aza-bicyclo[3.2.1-]octane-8-carboxylic acid tert-butyl ester (265 mg, 0.80 mmol) for (±)-3-exo-benzyl-2-endo-methoxy-8-aza-bicyclo[3.2.1]octane-8-carboxylic acid tert-butyl ester, the product (180 mg, 97%) was obtained as a yellow oil.

Mass spec.: 232.3 (M+1). $^1$H NMR (CDCl$_3$) 3.32 (3H, s, —OCH$_3$).

Step 5:

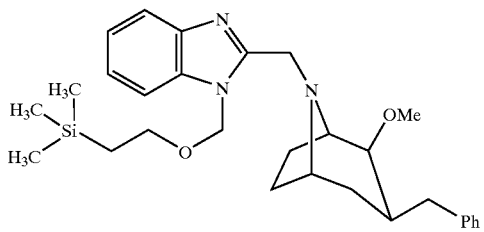

(±)-2-(3-exo-Benzyl-2-exo-methoxy-8-aza-bicyclo
[3.2.1]oct-8-ylmethyl)-1-(2-trimethylsilanyl-
ethoxymethyl)-1H-benzimidazole Employing the procedure substantially as described for (±)-3-exo benzyl-8-[1-(2-trimethylsilanyl-ethoxymethyl)-1H-benzimidazol-2-ylmethyl]-8-aza-bicyclo[3.2.1]octan-2-endo-ol, but substituting (±)-3-exo-benzyl-2-exo-methoxy-8-aza-bicyclo[3.2.1]octane for (±)-3-exo-benzyl-8-azabicyclo[3.2.1]octan-2-endo-ol: $^1$H NMR (CDCl$_3$) 7.76 (1H, d, J 8 Hz), 7.53 (1H, d, J 8 Hz), 7.29 (4H, m), 7.18 (3H, m), 6.15 (1H, d, J, 11 Hz), 6.01 (1H, d, J, 11 Hz), 3.90 (2H, dd, J 24, 13 Hz), 3.62 (2H, t, J, 8 Hz), 3.50 (1H, m), 3.26 (1H, s), 3.09 (3H, s), 2.77 (1H, m), 2.73 (1H, m), 2.48 (1H, dd, J 13, 6.5 Hz), 2.10 (2H, m), 1.89 (1H, m), 1.62 (2H, m), 1.37 (2H, m), 0.95 (2H, t, J, 8 Hz), 0.04 (9H, s).
Step 6:

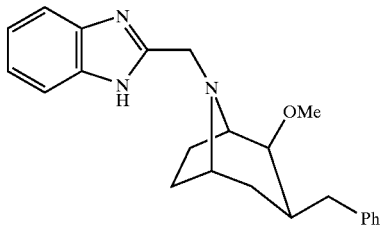

(±)-2-(3-exo-Benzyl-2-exo-methoxy-8-aza-bicyclo [3.2.1]oct-8-ylmethyl)-1H-benzimidazole The procedure followed was substantially as described in Step 7, Example 28: m.p. 172–173° C.

$^1$H NMR (DMSO-d$_6$) 10.76 (1H, br, s), 7.69 (1H, br s), 7.44 (1H, br s), 7.27 (3H, m), 7.19 (4H, m), 3.82 (2H, s), 3.30 (2H, m), 3.29 (3H, d, J 1 Hz), 2.84 (1H, m), 2.78 (1H, dd, J 13, 8 Hz), 2.60 (1H, dd, J 13, 7 Hz), 2.00 (3H, m), 1.79 (1H, m), 1.66 (1H, m), 1.42 (2H, m). Mass spec.: 362.4 (M+1). Analysis calculated for C$_{23}$H$_{27}$N$_3$O C, 76.42; H, 7.53; N, 11.94. Found: C, 77.17; H, 7.43; N, 11.94.

What is claimed is:

1. A compound having the formula:

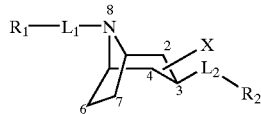

or a pharmaceutically acceptable salt thereof, wherein
R$_1$ is benzimidazolyl;
R$_2$ is phenyl, optionally substituted with one to five substituents, each substituent independently being chloro, fluoro, bromo, C$_1$–C$_4$alkyl, trifluoromethyl, hydroxy, or carboxy;
L$_1$ and L$_2$ are independently C$_1$–C$_4$alkyl, C$_1$–C$_4$alkenyl, C$_1$–C$_4$alkynyl, C$_1$–C$_4$alkoxy, aminoC$_1$–C$_4$alkyl, hydroxyC$_1$–C$_4$alkyl, carbonyl, cycloC$_3$–C$_6$alkyl or aminocarbonyl; and
optionally substituted at any of the 2, 3, 4, 6, or 7 positions independently with X, wherein X is hydroxy, amino, C$_1$–C$_4$alkylamino, di(C$_1$–C$_4$)alkylamino, C$_1$–C$_4$alkyl, —C(O)OC$_1$–C$_4$alkyl, —OCOOC$_1$–C$_4$alkyl, —NHCOOC$_1$–C$_4$alkyl, —OCONHC$_1$–C$_4$alkyl, carbonate, or -C$_1$–C$_4$alkylOC$_1$–C$_4$alkyl.

2. The compound according to claim 1, wherein said compound is
2-[3-(4-Chloro-benzyl)-8-aza-bicyclo[3.2.1]oct-8-ylmethyl]-1H-benzimidazole;
2-(3-Benzyl-8-aza-bicyclo[3.2.1]oct-8-ylmethyl)-1H-benzimidazole;
2-[3-(2-Fluoro-benzyl)-8-aza-bicyclo[3.2.1]oct-8-ylmethyl]-1H-benzimidazole;
2-[3-(4-Fluoro-benzyl)-8-aza-bicyclo[3.2.1]oct-8-ylmethyl]-1H-benzimidazole;
2-[3-(4-Methyl-benzyl)-8-aza-bicyclo[3.2.1]oct-8-ylmethyl]-1H-benzimidazole;
2-[3-(2-Methyl-benzyl)-8-aza-bicyclo[3.2.1]oct-8-ylmethyl]-1H-benzimidazole;
2-[3-(3-Methyl-benzyl)-8-aza-bicyclo[3.2.1]oct-8-ylmethyl]-1H-benzimidazole;
2-[3-(3-Fluoro-benzyl)-8-aza-bicyclo[3.2.1]oct-8-ylmethyl]-1H-benzimidazole;
2-[3-(4-Methoxy-benzyl)-8-aza-bicyclo[3.2.1]oct-8-ylmethyl]-1H-benzimidazole;
2-[3-(3-Chloro-benzyl)-8-aza-bicyclo[3.2.1]oct-8-ylmethyl]-1H-benzimidazole;
2-[3-(3,4-Dichloro-benzyl)-8-aza-bicyclo[3.2.1]oct-8-ylmethyl]-1H-benzimidazole;
8-(1H-Benzimidazol-2-ylmethyl)-3-benzyl-8-aza-bicyclo[3.2.1]octan-6-ol;
8-(1H-Benzimidazol-2-ylmethyl)-8-aza-bicyclo[3.2.1] octane-3-carboxylic acid 2-fluorobenzylamide;
2-[3-(3-Benzyl-8-aza-bicyclo[3.2.1]oct-8-yl)-propyl]-1H-benzimidazole;
(+)8-(1H-Benzimidazol-2-ylmethyl)-3-exo-benzyl-8-aza-bicyclo[3.2.1]octan-2-endo-ol;
(−)8-(1H-Benzimidazol-2-ylmethyl)-3-exo-benzyl-8-aza-bicyclo[3.2.1]octan-2-endo-ol;
(+)8-(1H-Benzimidazol-2-ylmethyl)-3-exo-benzyl-8-aza-bicyclo[3.2.1]octan-2-exo-ol;
(−)8-(1H-Benzimidazol-2-ylmethyl)-3-exo-benzyl-8-aza-bicyclo[3.2.1]octan-2-exo-ol;
(±)-2-(3-exo-Benzyl-2-endo-methoxy-8-aza-bicyclo[3.2.1]oct-8-ylmethyl)-1H-benzimidazole; or
(±)-2-(3-exo-Benzyl-2-endo-methoxy-8-aza-bicyclo[3.2.1]oct-8-ylmethyl)-1H-benzimidazole.

3. The compound according to claim 1, wherein said compound is

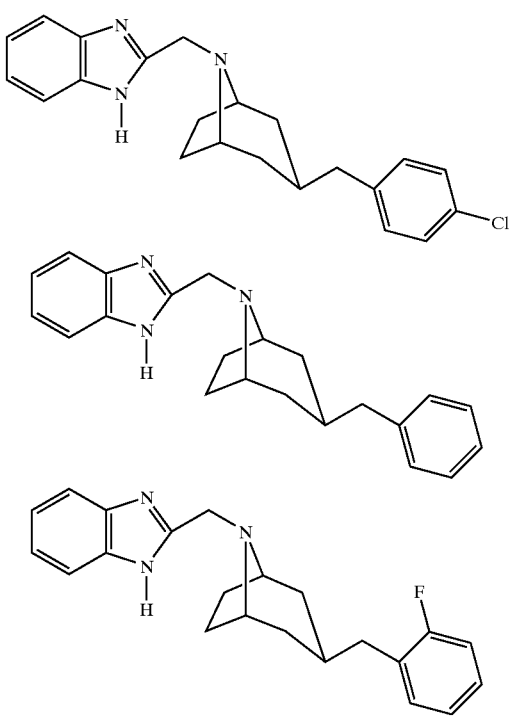

-continued
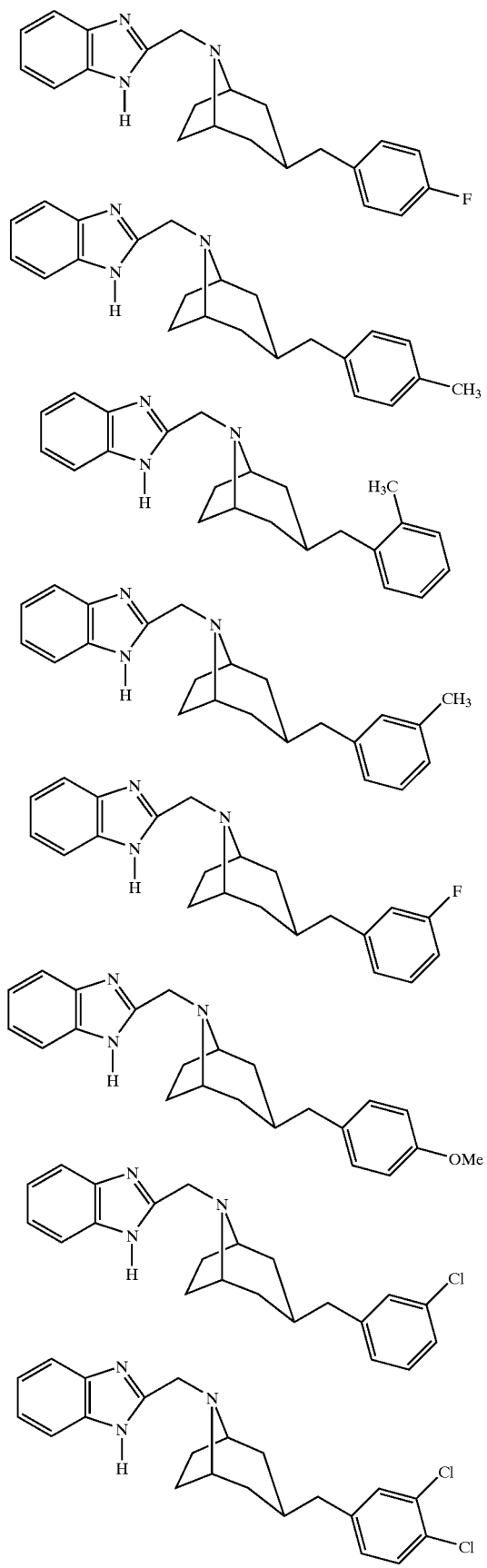
-continued
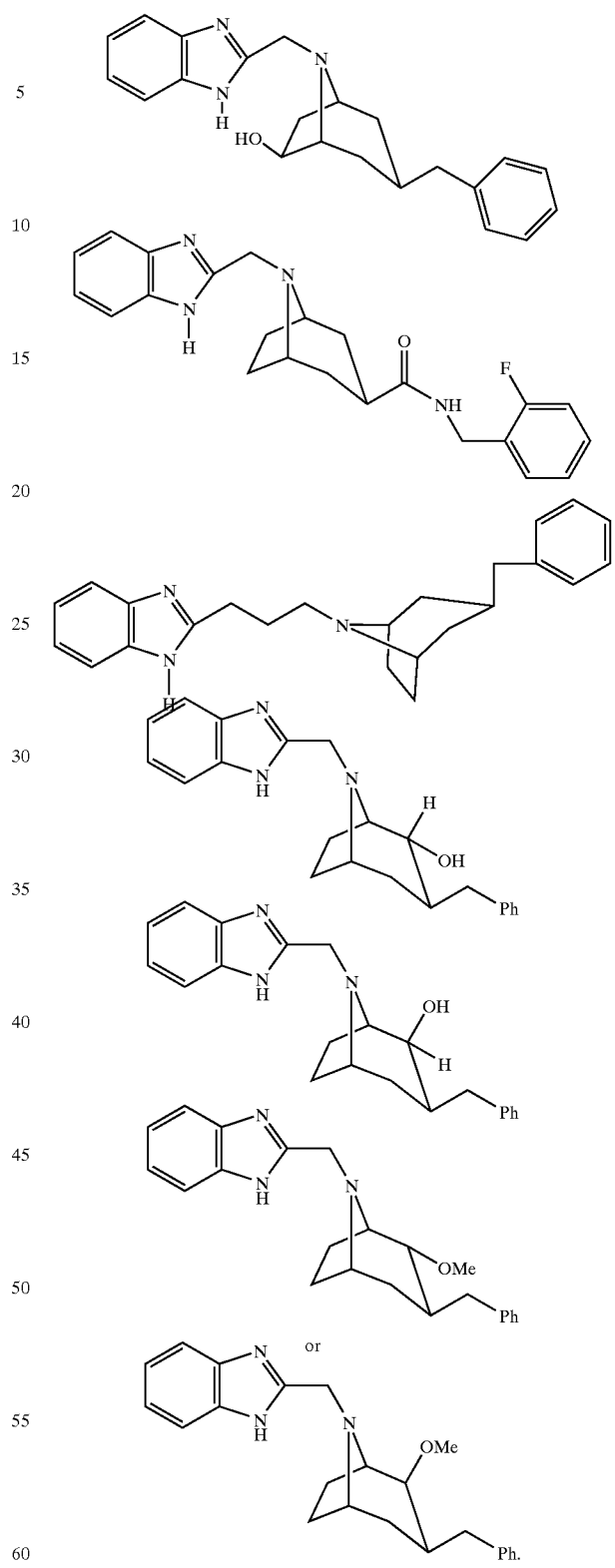
4. A pharmaceutical composition comprising an inert carrier and an effective amount of a compound according to claim 1.
* * * * *